US008920626B2

(12) United States Patent
Suzuki et al.

(10) Patent No.: US 8,920,626 B2
(45) Date of Patent: Dec. 30, 2014

(54) METHOD OF ELECTROCHEMICALLY DETECTING A SAMPLE SUBSTANCE

(75) Inventors: Seigo Suzuki, Ashiya (JP); Masayoshi Seike, Kobe (JP); Shigeki Iwanaga, Kobe (JP); Nobuyasu Hori, Kobe (JP); Hiroya Kirimura, Kobe (JP)

(73) Assignee: Sysmex Corporation, Hyogo (JP)

( * ) Notice: Subject to any disclaimer, the term of this patent is extended or adjusted under 35 U.S.C. 154(b) by 321 days.

(21) Appl. No.: 13/306,710

(22) Filed: Nov. 29, 2011

(65) Prior Publication Data

US 2012/0132543 A1  May 31, 2012

(30) Foreign Application Priority Data

Nov. 30, 2010  (JP) ................................. 2010-266819

(51) Int. Cl.
*G01N 27/00* (2006.01)
*G01N 33/543* (2006.01)

(52) U.S. Cl.
CPC .................................. *G01N 33/5438* (2013.01)
USPC ...................................... 205/775; 435/287.2

(58) Field of Classification Search
CPC ........... G01N 27/3275; G01N 27/3276; C12Q 1/6813; C12Q 1/6841
USPC ......... 435/287.1–288.7, 6.1–6.19; 205/780.5, 205/775
See application file for complete search history.

(56) References Cited

U.S. PATENT DOCUMENTS

| 2002/0052051 | A1 | 5/2002 | Egashira |
| 2002/0121314 | A1 | 9/2002 | Tao et al. |
| 2006/0078912 | A1 | 4/2006 | Bard et al. |
| 2008/0292545 | A1* | 11/2008 | Lin et al. ...................... 424/1.29 |
| 2010/0112578 | A1 | 5/2010 | Iwanaga |

FOREIGN PATENT DOCUMENTS

| EP | 0125139 | A2 | 11/1984 |
| EP | 2458383 | A1 | 5/2012 |
| FR | 2816058 | A1 | 5/2002 |
| GB | 2 462 062 | A | 1/2010 |
| WO | 9932662 | A1 | 7/1999 |

OTHER PUBLICATIONS

Harrison et al. Journal of Molecular Biology, 1963, 404-422.*
Mao et al: "Copper-enhanced gold nanoparticle tags for electrochemeical stripping detection of human IgG". Talanta, Elsevier, Amsterdam, NL, vol. 73. No. 3., Sep. 6, 2007, pp. 420-424.

* cited by examiner

*Primary Examiner* — Luan Van
*Assistant Examiner* — Gurpreet Kaur
(74) *Attorney, Agent, or Firm* — Sughrue Mion, PLLC

(57) ABSTRACT

A sample substance S is captured by a capture substance 10 which is immobilized on a working electrode body 161 to provide a method of electrochemically detecting a sample substance capable of detecting the sample substance with high sensitivity. A complex which includes, on a soluble carrier 21, a sample substance S and a labeled binder 20 that has a modified labeled substance 23 containing a labeled substance 20 bound to modified labeled substance 23 containing a labeled substance 24 and a binder 22 that binds to the sample substance S, formed on the working electrode 161. The soluble carrier 21 is dissolved, and the modified labeled substance 23 is attracted to the working electrode 161.

14 Claims, 21 Drawing Sheets

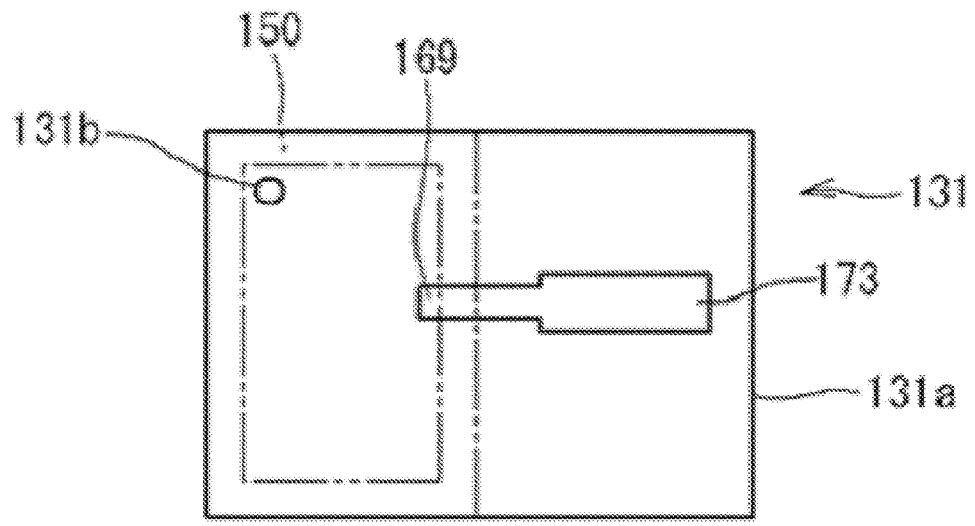
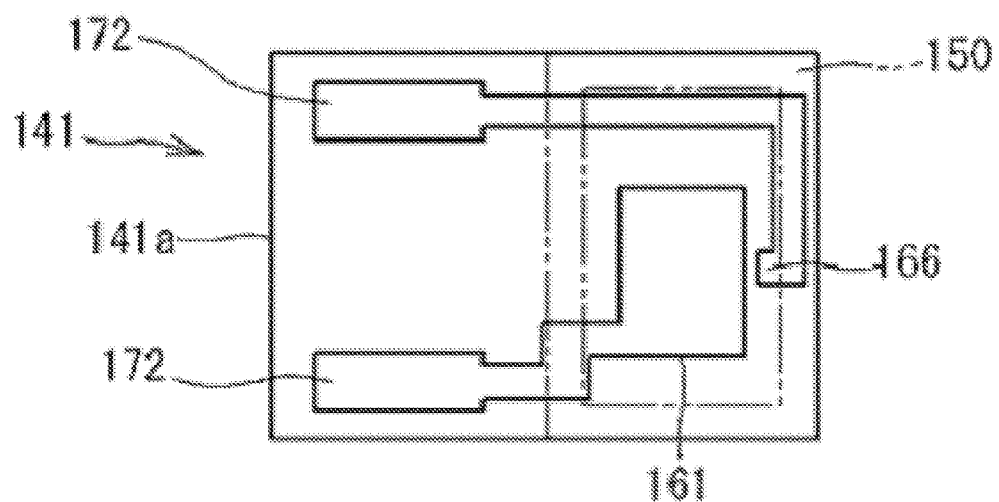

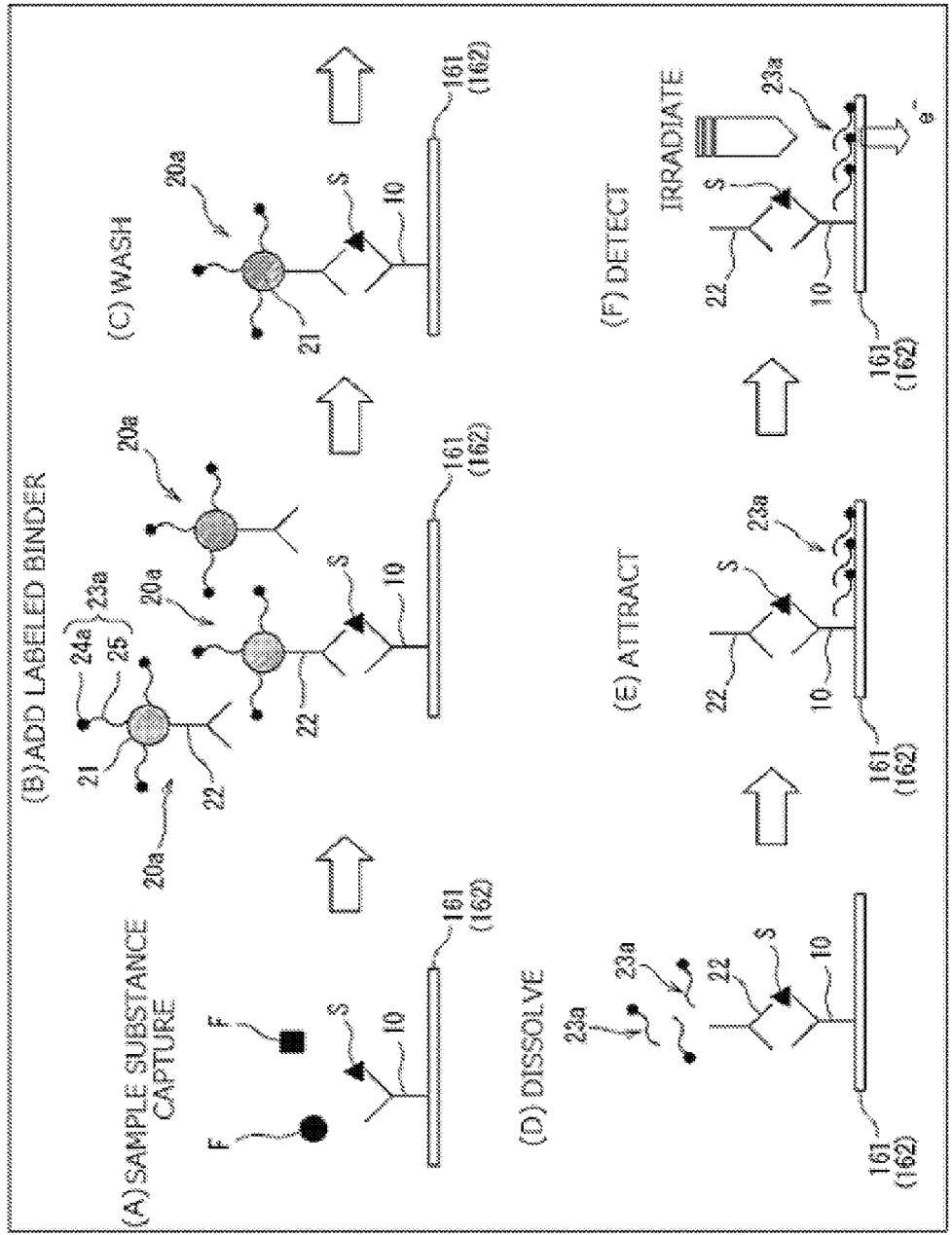

METHOD OF ELECTROCHEMICALLY DETECTING A SAMPLE SUBSTANCE

FIELD OF THE INVENTION

The present invention relates to a method of electrochemically detecting a sample substance. More specifically, the present invention relates to a method of electrochemically detecting a sample substance to be used for detection and quantification of a sample substance such as nucleic acid, protein and the like, and for clinical examination and diagnosis of disease using same.

BACKGROUND

Clinical examination and diagnosis of disease are carried out by detecting disease-related genes and proteins contained in biological samples using methods such as gene detection, immunological detection and the like. Electrochemical detection methods for sample substances are known as methods for clinical examination and diagnosis. Specifically, methods used for the detection of sample substances such as genes and proteins have been proposed which use electrical current generated by photoexcitation of a photochemically active labeled material, and current generated by photoexcitation or light generated by a voltage applied to an electrochemically active labeled substance.

When detecting a sample substance within a sample for clinical examination and diagnosis, the minute amount of sample substance within the sample must be detected with high sensitivity. For example, U.S. Patent Publication No. 2006/078912 discloses a method of detecting a sample substance using carrier particles which have a probe that binds to the sample substance and a plurality of electrochemically active ECL. When detecting electrochemiluminescence (ECL), the carrier is dissolved and dispersed by ECL release. Hence, contact efficiency between ECL and electrolyte is improved, which improves detection sensitivity. Therefore, development of a method of electrochemical detection capable of detecting a sample substance with higher sensitivity is desirable.

SUMMARY OF THE INVENTION

The scope of the present invention is defined solely by the appended claims, and is not affected to any degree by the statements within this summary.

In view of the preceding information, an object of the present invention is to provide a method of electrochemical detection capable of detecting a sample substance with higher sensitivity than the conventional art.

As a result of intensive investigation, the present inventors have discovered solutions to the aforesaid problems by:

(1) forming a complex which includes a sample substance and a labeled binder that has a soluble carrier bound to modified labeled substance containing a labeled substance and a binder that binds to the sample substance;

(2) dissolving the soluble carrier containing the labeled binder in the complex;

(3) attracting the modified labeled substance onto a working electrode. That is, the present inventors have discovered that a sample substance can be electrochemically detected with high sensitivity by obtaining signals with high efficiency based on a labeled substance that corresponds to the amount of the sample substance regardless of the size of the sample substance by performing the operations described in (1) through (3) above when electrochemically detecting a sample substance.

The present invention is based on the findings of these inventors.

An aspect of the present invention is a method of electrochemically detecting a sample substance, comprising:

contacting and capturing a sample containing a sample substance on a working electrode;

forming, a complex including a sample substance and a labeled substance on a working electrode by bringing a sample substance into contact with a labeled binder which has a soluble carrier bound to a modified labeled substance containing a labeled substance and a binder for binding to the sample substance, on a working electrode possessing the captured sample substance;

isolating the modified labeled substance by dissolving the soluble carrier contained in the complex formed on the working electrode;

attracting the modified labeled substance onto the working electrode; and electrochemically detecting the labeled substance in the modified labeled substance.

The method of detecting a sample substance of the present invention provides an electrochemical detection method capable of detecting a sample substance with greater sensitivity than the conventional art.

BRIEF DESCRIPTION OF THE DRAWINGS

FIG. 10A is a plan view of a modification of the top substrate;

FIG. 10B is a plan view of a modification of the bottom substrate;

FIG. 13 is a process chart showing the processing sequence of an embodiment of the method of electrochemical detection (photoelectrochemical detection method) of a sample substance of the present invention.

DETAILED DESCRIPTION OF THE PREFERRED EMBODIMENTS

The preferred embodiments of the present invention will be described hereinafter with reference to the drawings.
[Definition of Terms]

The description of the embodiments of the present invention are preceded by a definition of the terms used in the specification.

In the present specification, a capture substance ("10" in FIG. 1) is a substance for capturing a sample substance S, and is referred to as a substance which is immobilized on the working electrode 161.

Figure 1:
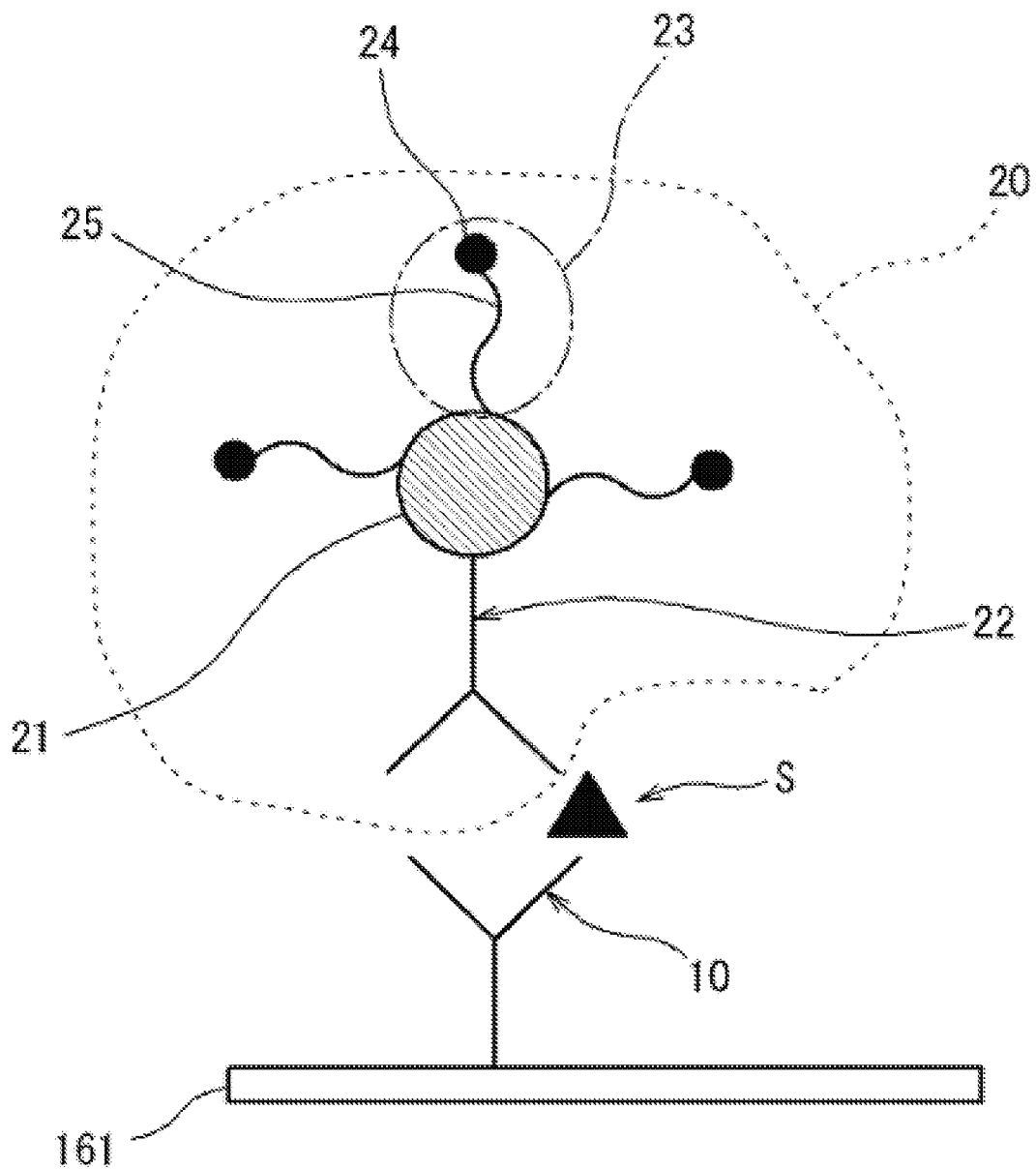
FIG. 1 is a brief illustration of a complex including a labeled binder, sample substance, and capture substance formed on a working electrode in an embodiment of the method of electrochemical detection of a sample substance of the present invention.

A labeled binder ("20" in FIG. 1) is a substance which contains a soluble carrier ("21" in FIG. 1), a modified labeled substance ("23" in FIG. 1), and a binder ("22" in FIG. 1). In the labeled binder 20 shown in FIG. 1, the modified labeled substance 23 and the binder 22 are immobilized on the soluble carrier 21.

The binder 22 is a substance which captures a sample substance S by immobilizing it on the soluble carrier 21.

The modified labeled substance ("23" in FIG. 1) contains a labeled substance ("24" in FIG. 1) which is attracted to the working electrode. The concept of the term "modified labeled substance" includes substances configured by a labeled substance ("24" in FIG. 1) and an attractant substance ("25" in FIG. 1). When a labeled substance ("24" in FIG. 1) in this state is attracted to a working electrode, the concept of the term "modified labeled substance" includes an individual labeled substance alone.
[Structure of the Detection Device]

An example of a detection device which uses the method of electrochemical detection of a sample substance of the present invention is described below with reference to the accompanying drawings.

Figure 2:
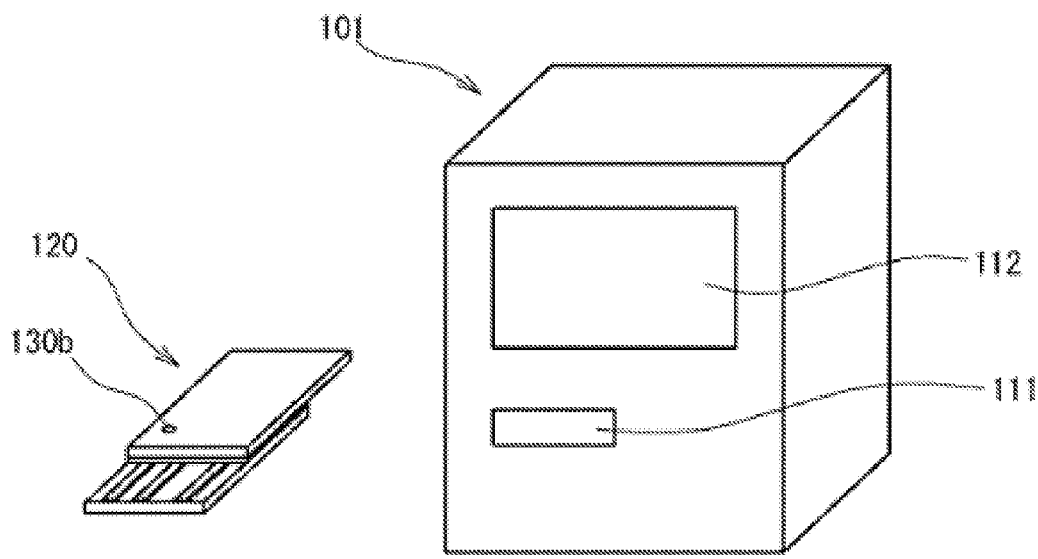
FIG. 2 is a schematic view showing a detection device using the method of electrochemical detection of a sample substance of an embodiment of the present invention.

FIG. 2 is a schematic view showing a detection device using the method of electrochemical detection of a sample substance of an embodiment of the present invention. The detection device 101 uses a photochemically active substance as a labeling substance in an electrochemical detection method to photoelectrochemically detect a sample substance.

The detection device 101 is provided with a chip receiver 111 for inserting the inspection chip 120, and a display 112 for displaying the detection result.

Figure 3:
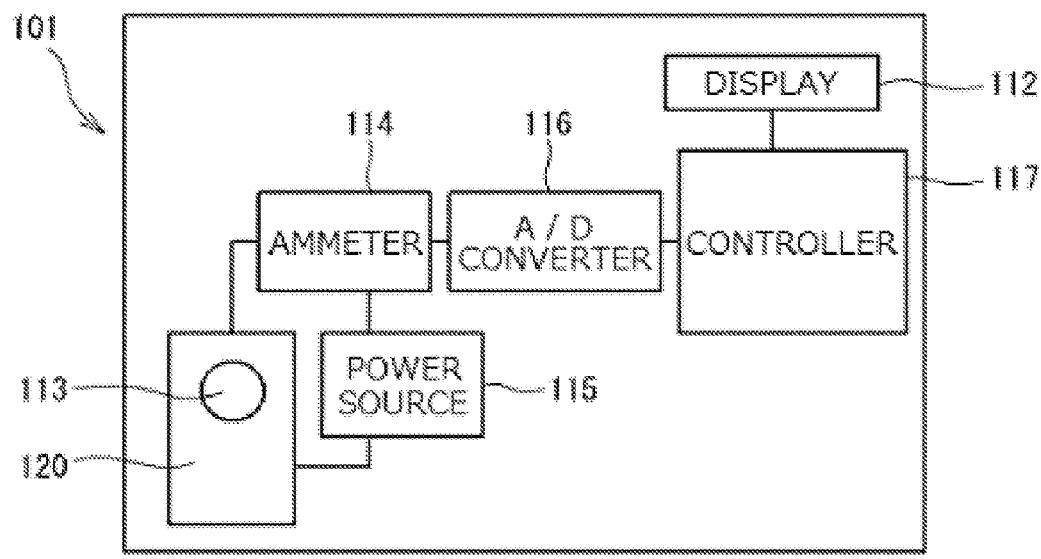
FIG. 3 is a block diagram showing the structure of the detection device in FIG. 2.

FIG. 3 is a block diagram showing the structure of the detection device in FIG. 2. The detection device 101 is provided with a light source 113, an ammeter 114, a power source 115, an A/D converter 116, a controller 117, and the display 112.

The light source 113 emits light which irradiates the labeled substance present on the working electrode of the inspection chip 120 to excite the labeled substance. The light source 113 may be a light source which generates excitation light. Fluorescent light, black light, germicidal lamp, incandescent lamp, low pressure mercury lamp, high pressure mercury lamp, xenon lamp, mercury-xenon lamp, halogen lamp, metal halide lamp, LED (white LED, blue LED, green LED, red LED and the like), laser light (carbon dioxide gas laser, dye laser, semiconductor laser), sunlight and the like may be used as the light source. Among these light sources, fluorescent lamp, incandescent lamp, xenon lamp, halogen lamp, metal halide lamp, LED, laser, or sunlight are preferable. Among these light sources, lasers are most preferable. The light source also may emit only light of a specific wavelength band via a splitter and bandpass filter as necessary.

The ammeter 114 measures the current flowing within the inspection chip 120 originating from the electrons released from the excited labeled substance.

The power source 115 supplies a predetermined potential to the electrode provided on the inspection chip 120.

The A/D converter 116 performs digital conversion of the photocurrent value measured by the ammeter 114.

The controller 117 is configured by a CPU, RAM, ROM and the like, and controls the operation of the display 112, light source 113, ammeter 114, and power source 115. The controller 117 estimates the amount of labeled substance from the photocurrent value obtained from the digital conversion by the A/D converter 116 based on a previously prepared calibration curve showing the relationship between amount of test substance and the photocurrent, and calculates the amount of sample substance therefrom.

The display 112 then displays the amount of labeled substance estimated by the controller 117.

Note that, in the present invention, the detection device need not be provided with the light source 113 when detection of the labeled substance is performed according to a method using redox current electrochemiluminescence detection (to be described later) (not shown in the drawings).

When detecting a test substance which contains a labeled substance via electrochemiluminescence, the detection device may be further provided with a sensor for detecting light or the light generated from the labeled substance.

[Structure of the Inspection Chip]

Figure 4:
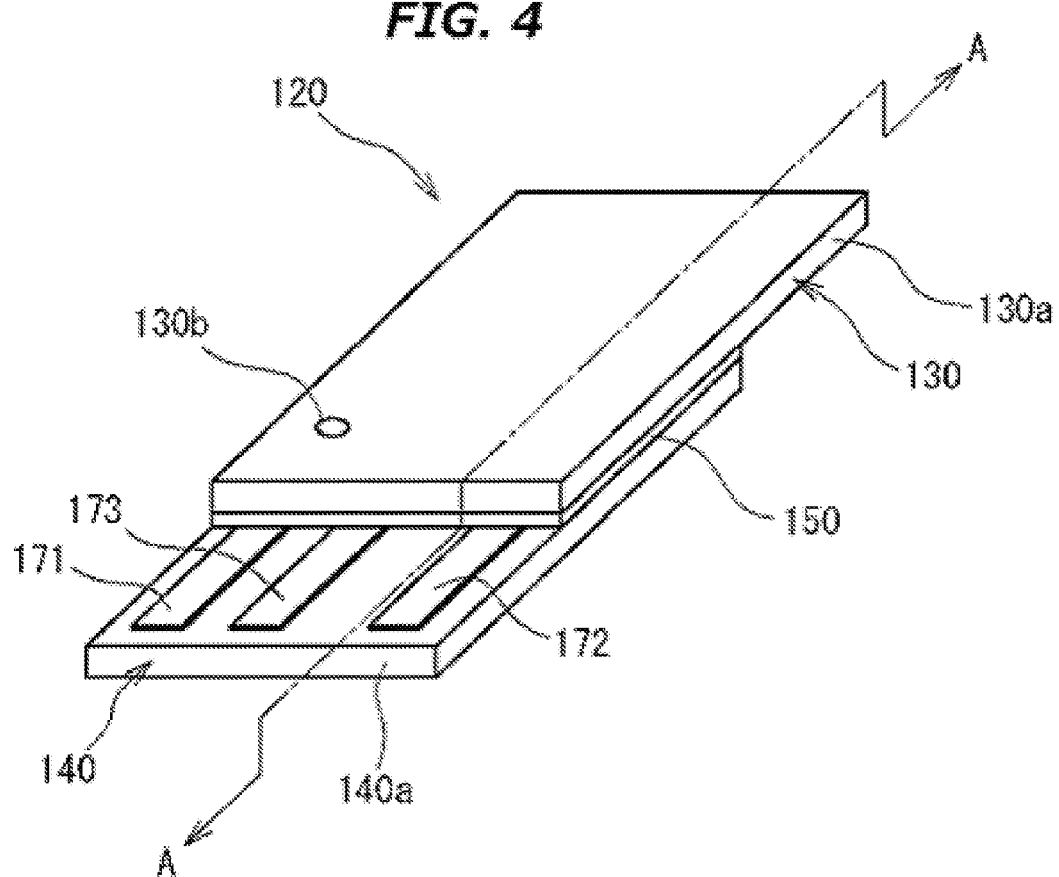
FIG. 4 is a schematic view showing a detection chip used in the method of electrochemical detection of a sample substance of an embodiment of the present invention.
Figure 5:
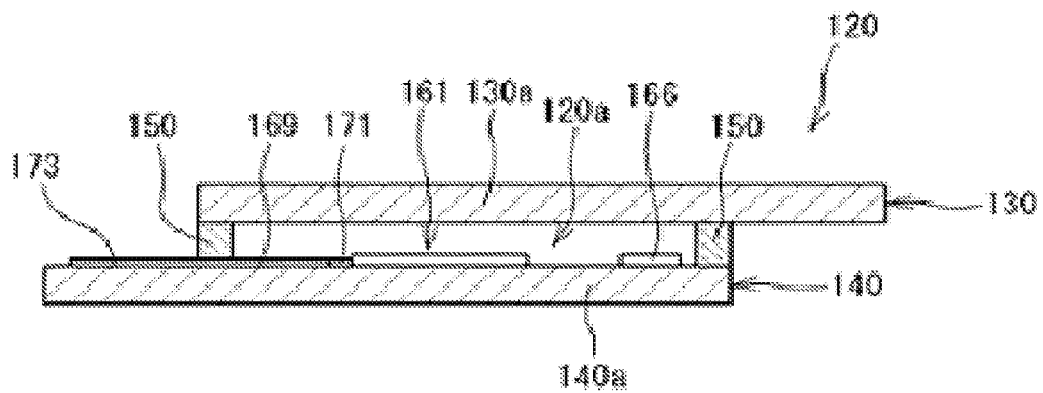
FIG. 5 is a cross sectional view on the A-A line of the inspection chip in FIG. 4.

The structure of the inspection chip 120 is described below as it is used in the method of electrochemical detection of a sample substance of the embodiment of the present invention. FIG. 4 is a schematic view showing a detection chip used in the method of electrochemical detection of a sample substance of an embodiment of the present invention. FIG. 5 is a cross sectional view on the A-A line of the inspection chip in FIG. 4.

The inspection chip 120 is provided with a top substrate 130, a bottom substrate (electrode substrate) 140 which is disposed below the top substrate 130, and an interval holding member 150 which is interposed between the top substrate 130 and the bottom substrate 140. In the inspection chip 120, the top substrate 130 and the bottom substrate 140 are arranged so as to overlap on one side. The interval holding member 150 is interposed at the overlapping part of the top substrate 130 and the bottom substrate 140.

Figure 6A:
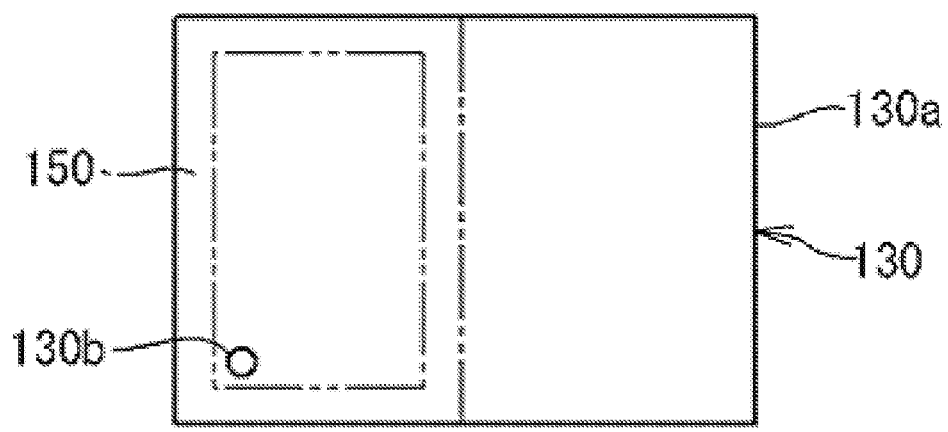
FIG. 6A is a perspective view of the top substrate of the inspection chip of FIG. 4 as seen from the bottom side.

The top substrate 130 is configured by a substrate main body 130a as shown in FIG. 6A. The substrate main body 130a has a sample injection inlet 130b for injecting a sample containing the test substance into the interior. The sample injection inlet 130b is on the inner side of the substrate main body 130a from the part where the interval holding member 150 is interposed.

The substrate main body 130a is formed in a rectangular shape. Note that the shape of the substrate main body 130a is not specifically limited and also may be polygonal-shaped, disk-shaped or the like. From the perspective of ease of fabrication and handling of the substrate, a rectangular shape is preferable. The material constituting the substrate body 130a is not specifically limited, and may be, for example, glass, plastics such as polyethylene terephthalate, polyimide resins, and inorganic materials such as metals. Among these materials, glass is preferable from the perspectives of optical transparency, adequate heat resistance, ensuring smoothness, and low material cost. From the perspective of ensuring sufficient durability, the thickness of the substrate main body 130a is preferably 0.01 to 1 mm, more preferably 0.1 to 0.7 mm, and most preferably about 0.5 mm. In addition, the size of the board body 130a is not specifically limited, but is usually about 20×20 mm depending on the number of items to be detected when detecting a wide variety of test substances and sample substances (many items).

Figure 6B:
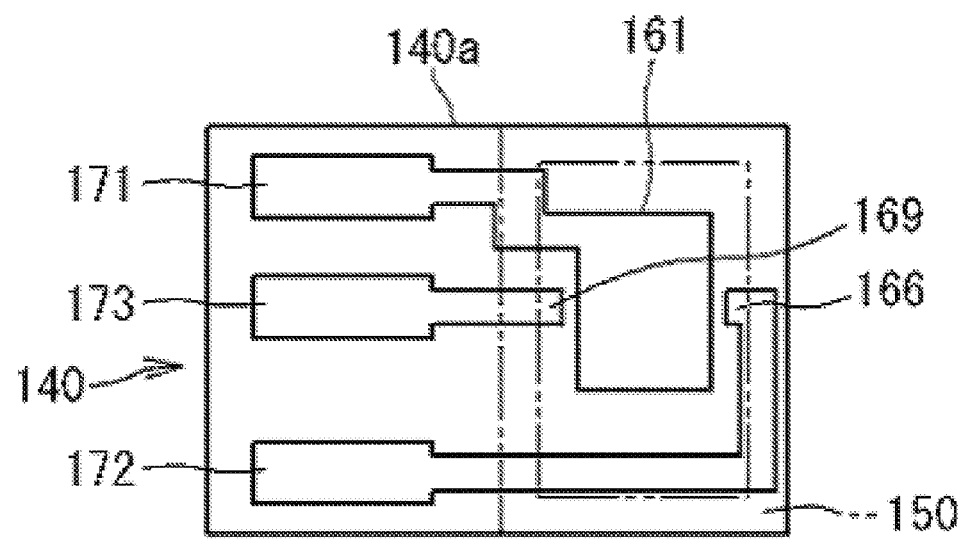
FIG. 6B is a perspective view of the top substrate of the inspection chip of FIG. 4 as seen from the top side.

The bottom substrate 140 has a substrate main body 140a, working electrode 161, counter electrode 168, and reference electrode 169 as shown in FIG. 6B. The substrate main body 140a has substantially the same rectangular shape and dimensions as the substrate main body 130a of the top substrate 130. The surface of the substrate main body 140a has a working electrode 161, an electrode lead 171 which is connected to the working electrode 161, a counter electrode 168, and lead electrode 172 which is connected to the counter electrode 168, a reference electrode 169, and an electrode lead 173 which is connected to the reference electrode 169.

The material constituting the substrate body 140a may be a material which is permeable to light. This material is not specifically limited, and may be, for example, glass, plastics such as polyethylene terephthalate, polyimide resins, and inorganic materials such as metals. Among these materials, glass is preferable from the perspectives of sufficient optical permeability, adequate heat resistance, ensuring smoothness, and low material cost. The material, size and thickness of the substrate body 140a is identical to the material, size and thickness of the substrate body 130a of the top substrate 130.

In the bottom substrate 140, the working electrode 161 is disposed on part of one side of the substrate body 140a (right side in FIG. 6B). The electrode lead 171 extends from the working electrode 161 toward the other side (left side in FIG. 6B) of the substrate main body 140a. The counter electrode 168 is disposed on the outer side from the working electrode 161 (right side of the working electrode 61 in FIG. 6B) on the substrate body 140a. The electrode lead 172 extends from the counter electrode 168 toward the other side (left side in FIG. 6B) of the substrate main body 140a and detours around the working electrode 161. The reference electrode 169 is positioned facing the counter electrode 166 with the working electrode 161 interposed therebetween. The electrode lead 173 extends from the reference electrode 169 toward the other side (left side in FIG. 6B) of the substrate main body 140a. The electrode lead 171 of the working electrode 161, the electrode lead 172 of the counter electrode 166, and the electrode lead 173 of the reference electrode 169 are arranged so as to be mutually parallel at the other end of the substrate main body 140a. The electrode leads 171, 172, and 173 extends from the overlapping part of the top substrate 130 and the bottom substrate 140 so as to be exposed to the outside.

The working electrode 161 is approximately square in shape.

Figure 7A:
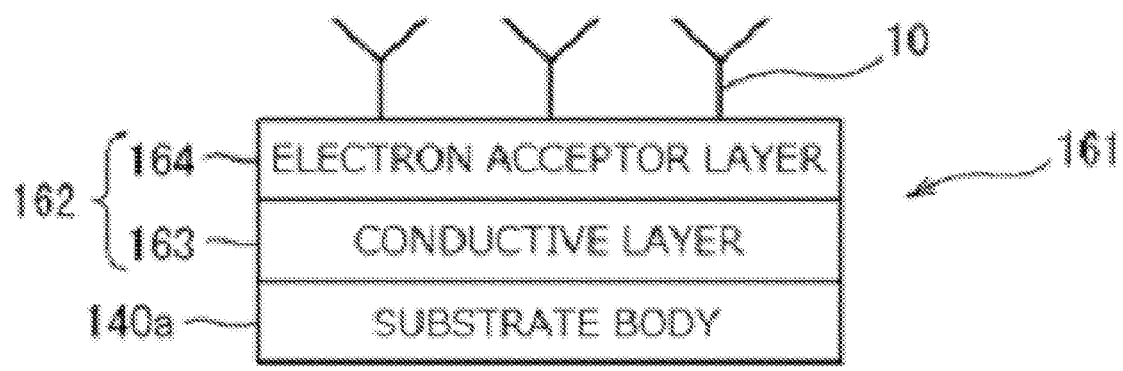
FIG. 7A is a cross sectional view schematically showing an example of a portion of a bottom substrate containing a working electrode used in the method of photoelectrochemical detection.

FIG. 7A is a cross sectional view schematically showing an example of a portion of a bottom substrate containing a working electrode used in the method of photoelectrochemical detection.

The working electrode 161 shown in FIG. 7A is configured by an electrode body 140a, and a working electrode body 162 formed on the substrate body 104a. A capture substance 10 is immobilized on the surface of the working electrode 162.

The working electrode body 162 is configured by a conductive layer 163, and an electron receptor layer 164 formed on the surface of the conductive layer 163.

The conductive layer 163 is formed of an electrically conductive material. Examples of useful conductive materials include metals such as gold, silver, copper, carbon, platinum, paladium, chrome, aluminum, nickel and the like or alloys containing at least one thereof; indium oxide, indium oxide-based materials such as indium oxide containing tin as a dopant; tin oxide, tin oxide-based materials such as tin oxide containing antimony as a dopant (ATO), tin oxide containing fluorine as a dopant (FTO) and the like; titanium, titanium-based materials such as titanium oxide, titanium nitride and the like; and carbon-based materials such as graphite, glassy carbon, pyrolytic graphite, carbon paste, carbon fiber and the like.

The thickness of the conductive layer 163 is preferably 1 to 1,000 nm, and more preferably 10 to 200 nm.

Note that the conductive material may be a composite substrate provided with a conductive layer configured by a conductive material disposed on the surface of a nonconductive substrate made of a nonconductive substance such as glass or plastic. The form of the conductive layer may be either a thin film or a spot. Examples of useful materials for constituting the conductive layer include tin-doped indium oxide (ITO), fluorine-doped tin oxide (FTO), antimony-doped tin oxide (ATO) and the like.

The conductive layer 163 may be formed by, for example, a film formation method according to the type of material configuring the conductive layer 163. Deposition method, sputtering, imprinting, screen printing method, plating method, sol-gel method, spin coating, dipping, vapor deposition and the like may be used as a film forming method.

The electron acceptor layer 164 contains a substance capable of accepting electrons (electron acceptor material). The electron acceptor material may be a substance may obtain an energy level by injection of electrons originating from a test substance by photoexcitation. In this case, "energy level by injection of electrons originating from a test substance by photoexcitation" means a conduction band when, for example, a semiconductor is used as the electron acceptor material. That is, the electron acceptor material may have a lower energy level than the lowest unoccupied molecular orbital (LUMO) of the labeled substance (described later).

The electron acceptor material is not specifically limited, and examples of useful materials include individual semiconductors such as silicon, germanium and the like; oxide semiconductors containing oxides of titanium, tin, zinc, iron, tungsten, zirconium, hafnium, strontium, indium, cerium, yttrium, lanthanum, vanadium, niobium tantalum and the like; perovskite-type semiconductors such as strontium titanate, calcium titanate, sodium titanate, vanadium titanate, potassium niobate and the like; sulfide semiconductors containing sulfides of cadmium, zinc, lead, silver, antimony, bismuth and the like; semiconductors containing nitrides of gallium, titanium and the like; semiconductors formed of selenide of cadmium, lead (for example, cadmium selenide and the like); semiconductors containing cadmium telluride; semiconductors containing phosphide of zinc, gallium, indium, cadmium and the like; semiconductors containing compounds of gallium arsenide, copper-indium-selenide, copper-indium-sulfide and the like; and organic semiconductors or compound semiconductors containing carbon. Note that these semiconductors also may be either true semiconductors or impure semiconductors.

Among these semiconductors, oxide semiconductors are preferable. Among true oxide semiconductors, titanium oxide, zinc oxide, tin oxide, niobium oxide, indium oxide, tungsten oxide, tantalum oxide, and strontium titanate are preferable. Among the impure oxide semiconductors, tin-doped indium oxide, and fluorine-doped tin oxide are preferable. Tin-doped indium oxide and fluorine-doped tin oxide combine the characteristics of both electron acceptor material and conductive material. These materials, therefore, may be used alone as the material forming the working electrode body.

The thickness of the electron acceptor layer 164 is usually 0.1 to 100 nm, and preferably 0.1 to 10 nm.

The electron acceptor layer 164 may be formed by a method similar to the methods used to form the conductive layer 163 depending on the type of material used to configure the electron acceptor layer 164.

Note that when the conductive layer 163 is a composite substrate, the electron acceptor layer 164 is formed on the conductive substrate.

A capture substance 10 for capturing the sample substance S is immobilized on the surface of the working electrode body 162 (surface of the electron acceptor layer 164). Hence, the sample substance S is induced to be present near the working electrode body 162.

The capture substance 10 may be suitably selected according to the type of sample substance S. Examples of useful capture substances 10 include nucleic acids, proteins, peptides, oligosaccharides, antibodies, and nano structures with specific recognition ability.

The fixed amount of capture substance 10 on the surface of the working electrode body 162 is not specifically limited. The fixed amount of capture substance 10 on the surface of the working electrode body 162 also may be set according to purpose and objective.

The fixation of the capture substance 10 on the surface of the working electrode body 162 is accomplished through a linkage group which chemically adheres to the working electrode body 162. Usable linking groups may include, for example, a thiol group, hydroxyl group, a phosphate group, a carboxyl group, carbonyl group, aldehyde, sulfonic acid, an amino group and the like. Fixation of the capture substance 10 on the surface of the working electrode body 162 also may be carried out by physical adsorption and photo-curable resin.

The working electrode body 162 also may be surface treated with silane coupling agent and the like. The surface of the working electrode body 162 can be suitably adjusted to be hydrophilic or hydrophobic via this surface treatment. Examples of useful silane coupling agent include cationic silane coupling agents such as aminopropyl triethoxysilane (APTES) and the like.

Figure 7B:
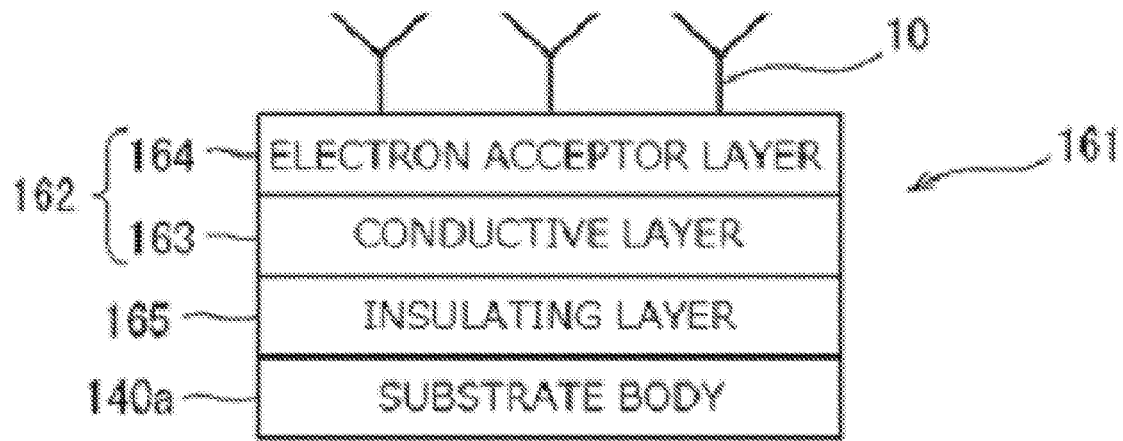
FIG. 7B is a cross sectional view schematically showing a modification of a portion of a bottom substrate containing a working electrode used in the method of photoelectrochemical detection.
Figure 8A:
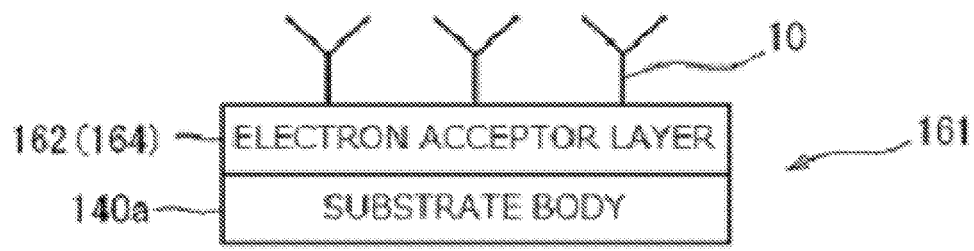
FIG. 8A is a cross sectional view schematically showing another modification of a portion of a bottom electrode containing a working electrode used in the method of photoelectrochemical detection.
Figure 8B:
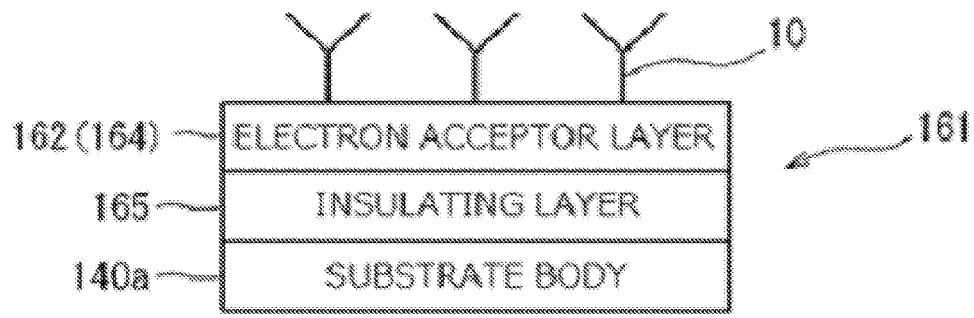
FIG. 8B is a cross sectional view schematically showing another modification of a portion of a bottom substrate containing a working electrode used in the method of photoelectrochemical detection.

FIGS. 7B, 8A, and 8B are cross sectional views of modifications of a portion of a bottom substrate containing a working electrode used in the method of photoelectrochemical detection.

As shown in FIG. 7B, in the present invention the conductive layer 163 also may be formed on and insulating layer 165 which is deposited on the surface of the substrate body 140a. In this case, the insulating layer 165, conductive layer 163, and electron acceptor layer 164 are sequentially formed on the surface of the substrate body 140a.

The insulating layer 165 is configured by an insulating material. The insulating material is not specifically limited and may be, for example, glass, plastic, or synthetic resin such as a fluororesin. The insulating layer 165 may be formed by a suitable method according to the type of insulating material. Examples of useful methods include sputtering, vapor deposition, screen printing method, spin coating, imprinting, spray coating and the like.

As shown in FIGS. 8A and 8B, in the present invention the working electrode body 162 also may be configured by an electron acceptor layer 164 alone when the electron acceptor layer 164 is configured by a material having the characteristics of both an electron acceptor material and a conductive material.

Figure 9A:
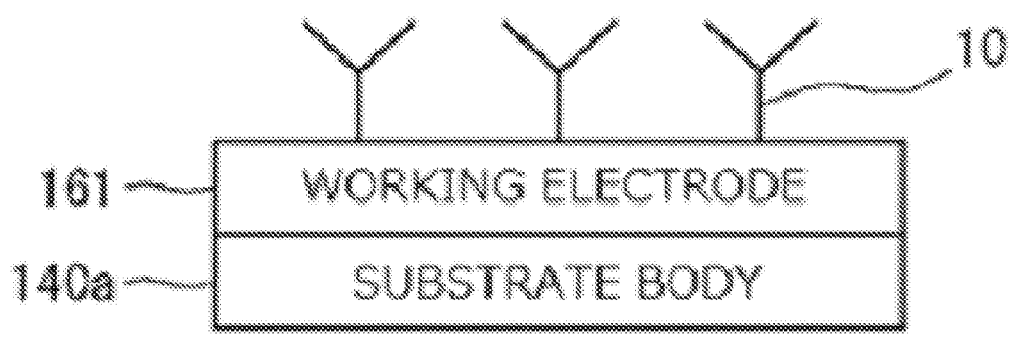
FIG. 9A is a cross sectional view schematically showing yet another modification of a portion of a bottom substrate containing a working electrode used in a method of redox current electrochemiluminescence detection.
Figure 9B:
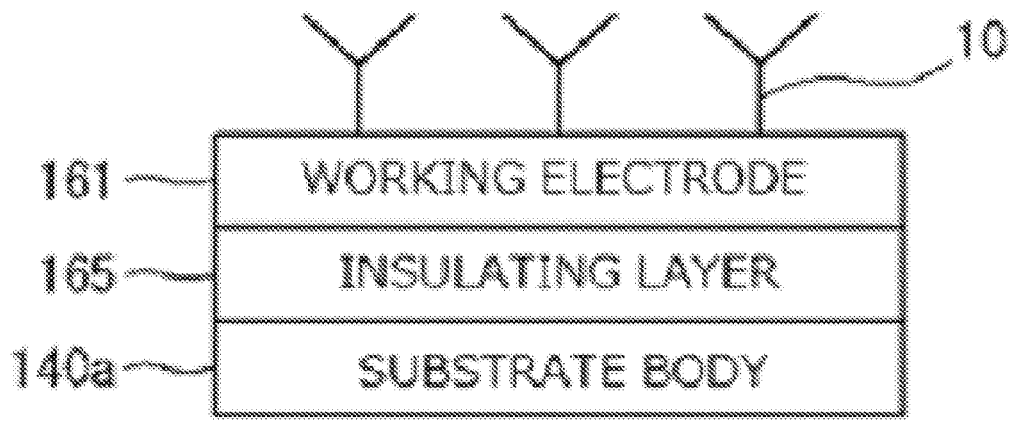
FIG. 9B is a cross sectional view schematically showing yet another modification of a portion of a bottom substrate containing a working electrode used in a method of redox current electrochemiluminescence detection.

FIG. 9A is a cross sectional view showing a modification of a portion of a bottom substrate containing a working electrode used in a method of redox current electrochemiluminescence detection. FIG. 9B is a cross sectional view showing a modification of a portion of a bottom substrate containing a working electrode used in a method of redox current electrochemiluminescence detection.

When the inspection chip is used in redox current electrochemiluminescence detection, the working electrode 161 is stable relative to the liquid used, that is, the electrode may be formed of conductive material (refer to FIGS. 9A and 9B). The electrode may be, for example, a carbon electrode formed of graphite, glassy carbon, pyrolytic graphite, carbon paste, carbon fiber and the like; noble metal electrode formed of platinum, black platinum, gold, palladium, rhodium and the like; oxide electrodes formed of titanium oxide, tin oxide, manganese oxide, lead oxide and the like; semiconductor electrodes formed of electron acceptor materials such as silicon, germanium, zinc oxide, cadmium sulfide, titanium dioxide, gallium arsenide and the like; and titanium electrodes made of titanium.

The counter electrode 166 is a thin layer composed of a conductive material. Examples of useful conductive materials include metals such as gold, solver, copper, carbon, platinum, palladium, chrome, aluminum, nickel and the like, or alloys containing at least one thereof, metal oxides such as ATO, FTO, conductive ceramics such as indium oxide and ITO, titanium, titanium compounds such as titanium oxide, titanium nitride and the like. The thickness of the thin film is preferably 1 to 1,000 nm, and more preferably 10 to 200 nm.

The reference electrode 169 is a thin layer composed of a conductive material. Examples of useful conductive materials include metals such as gold, solver, copper, carbon, platinum, palladium, chrome, aluminum, nickel and the like, or alloys containing at least one thereof, metal oxides such as ATO, FTO, conductive ceramics such as indium oxide and ITO, titanium, titanium compounds such as titanium oxide, titanium nitride and the like. The thickness of the thin film is preferably 1 to 1,000 nm, and more preferably 10 to 200 nm. Note that although the reference electrode 169 is provided in the present embodiment, the reference electrode 169 need not necessarily be provided in the present invention. Depending on the type and thickness of the electrode used in the counter electrode 166, the counter electrode 166 also may serve as the reference electrode 169 when measuring a current that has a very slight influence on a voltage drop (for example, 1 μA or less). On the other hand, when measuring a large current, the reference electrode 169 is preferable from the perspective of suppressing the voltage drop influence and stabilizing the voltage supplied to the working electrode 161.

Interval holding member 150 is formed in the shape of a rectangular ring, which is made of silicone rubber insulators. The interval holding member 150 is arranged so as to circumscribe the working electrode 161, counter electrode 166, and reference electrode 169 (refer to FIGS. 5 and 6). A gap is formed between the top substrate 130 and the bottom substrate 140, and the gap is equivalent to the thickness of the interval holding member 150. Hence, a space 120a is formed between the electrodes 161, 166, and 169 to accommodate a sample and electrolyte. The thickness of the interval holding member 150 is usually 0.2 to 300 μm. In the present invention, the material constituting the interval holding member 150 may be, for example, a double-sided tape of polyester film rather than silicone rubber.

[Structure of the Inspection Chip]

Figure 11A:
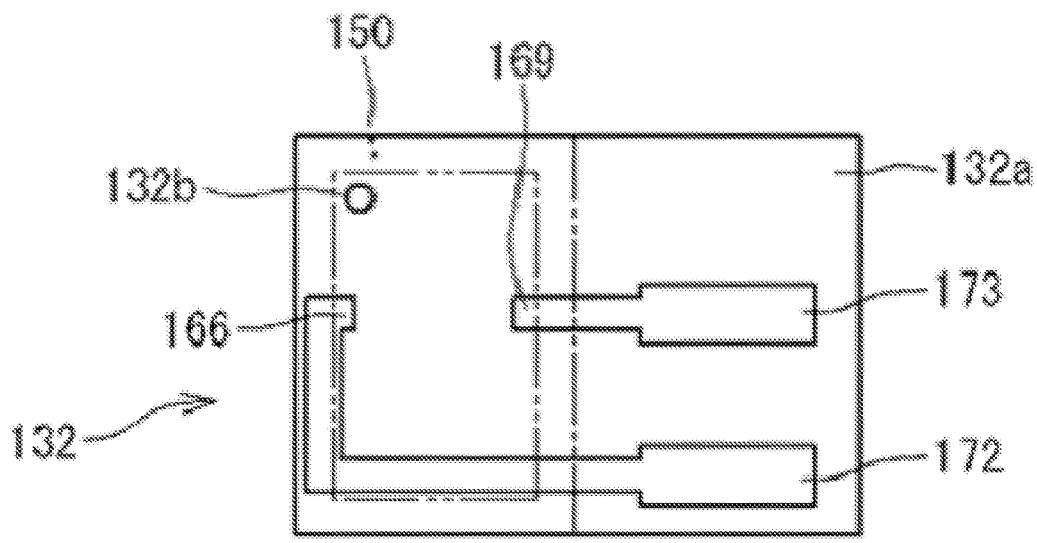
FIG. 11A is a plan view of a modification of the top substrate.
Figure 11B:
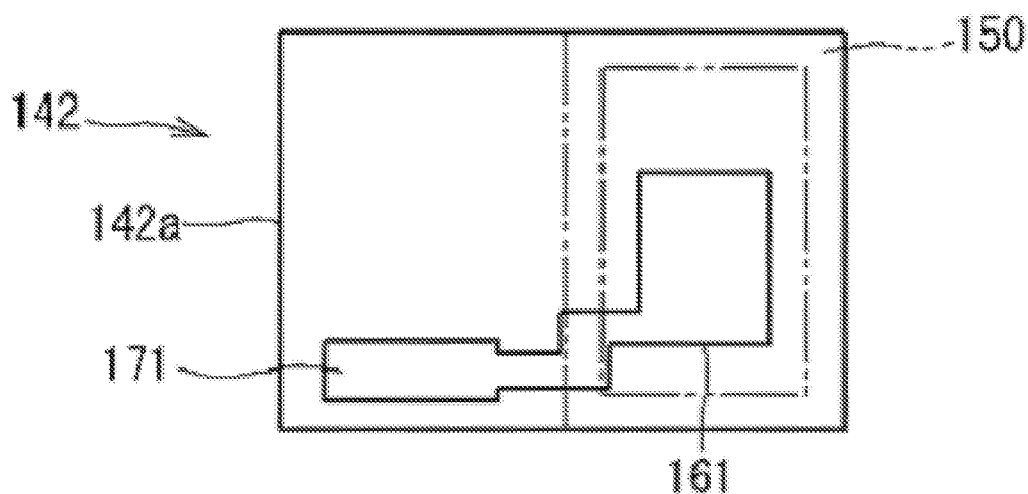
FIG. 11B is a plan view of a modification of the bottom substrate.

In the present invention, the working electrode 161, counter electrode 166, and reference electrode 169 may be disposed within the frame of the interval holding member 150 so that no electrode comes into contact with another electrode. Therefore, the working electrode 161, counter 166, and reference electrode 169 may be formed on different substrate bodies. That is, the inspection chip may have a top substrate 131 (refer to FIG. 10A) wherein a sample injection inlet 131b and reference electrode 169 are formed on a substrate body 131a, and a bottom substrate 141 (refer to FIG. 10B) wherein the working electrode 161 and counter electrode 166 are formed on the substrate body 141a. Further, the inspection chip may have a top substrate 132 (refer to FIG. 11A) wherein a sample injection inlet 132b, counter electrode 166, and reference electrode 169 are formed on a substrate body 132a, and a bottom substrate 142 (refer to FIG. 11B) wherein the working electrode 161 is formed on the substrate body 142a.

Figure 12A:
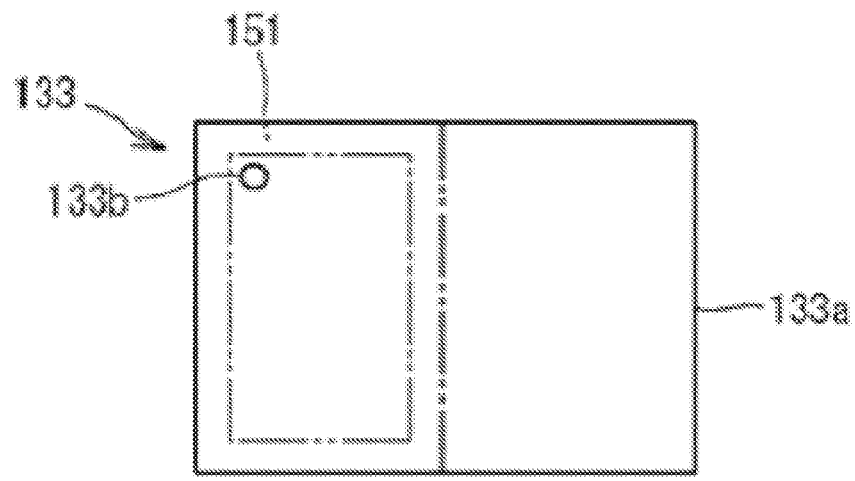
FIG. 12A is a plan view of a modification of the top substrate.
Figure 12B:
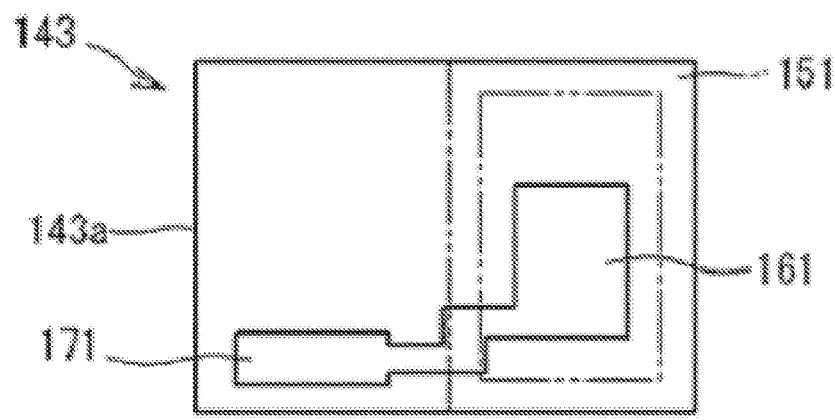
FIG. 12B is a plan view of a modification of the bottom substrate.
Figure 12C:
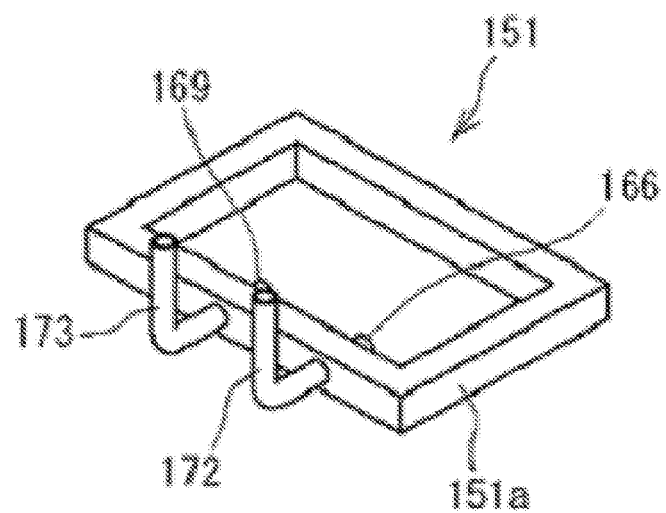
FIG. 12C is a perspective view illustrating the interval holding member.

In the present invention, the counter electrode 166 and the reference electrode 169 need not be thin film electrodes formed on a substrate body. That is, the inspection chip may have a top substrate 133 (refer to FIG. 12A) wherein a sample injection inlet 133b is formed on a substrate body 133a, a bottom substrate 143 (refer to FIG. 12B) wherein the working electrode 161 is formed on the substrate body 143a (refer to FIG. 12B), and an interval holding member 151 wherein the counter electrode 166 and the reference electrode 169 are provided on a member body 151a (refer to FIG. 12C). In this case, at least either the counter electrode 166 or the reference electrode 169 is provided on the member body of the interval holding member. The other electrodes, except those electrodes provided on the member body, may be provided on either the top substrate and bottom substrate.

[Method of Electrochemically Detecting a Sample Substance]

The method of electrochemically detecting a sample substance of the present invention includes:

(A) a capture step for contacting and capturing a sample containing a sample substance on a working electrode;

(B) a forming step for forming, a complex including a sample substance and a labeled substance on a working electrode by bringing a sample substance into contact with a labeled substance which has a soluble carrier bound to a modified labeled substance containing a labeled substance and a binder for binding to the sample substance on a working electrode possessing the captured sample substance;

(C) an isolating step for isolating the modified labeled substance by dissolving the soluble carrier contained in the complex formed on the working electrode;

(D) an attracting step for attracting the modified labeled substance onto the working electrode; and (E) a detecting step for electrochemically detecting the labeled substance within the modified labeled substance.

The method of the present invention has one aspect in performing (1) through (3) below.

(1) Forming the complex containing the labeled binder and the sample substance on the working electrode;

(2) dissolving the soluble carrier containing the labeled binder in the complex; and (3) attracting the modified labeled substance to the working electrode.

The modified labeled substance can be obtained in an amount corresponding to the sample substance by forming the complex. Electrons can be readily and efficiently received between the working electrode and the labeled substance by dissolving the soluble carrier and thereafter attracting the modified labeled substance onto the working electrode. The method of the present invention can therefore detect the labeled substance in an amount corresponding to the sample substance with high sensitivity.

In the method of the present invention, uses an electrochemically active or photochemically active substance as the labeled substance. An electrochemically active substance is detected using redox current or electrochemiluminescence based on the substance. A photochemically active substance, on the other hand, is detected using electrons released via photoexcitation of the substance. The method of the present invention, therefore, can be broadly divided into a photoelectrochemical method (refer to FIG. 13) and a redox current electrochemiluminescence method (FIG. 14) according to the type of detection mode to detect the labeled substance.

1. Photoelectrochemical Detection Method

The photoelectrochemical detection method is described first below. FIG. 13 is a process chart showing the processing sequence of an embodiment of the method of electrochemical detection (photoelectrochemical detection method) of a sample substance of the present invention. Although the detection device shown in FIG. 1 and the inspection chip shown in FIG. 4 are used in the photoelectrochemical detection method, the present invention is not limited to using these.

The inspection chip shown in FIG. 4 is used in the example described below.

In the photoelectrochemical detection method, first, a sample containing the sample substance S is injected into the inspection chip from the sample injection inlet 130$b$ of the inspection chip 120. The sample substance S is then captured on the working electrode 161 (refer to step (A) and FIG. 13(A)). In step (A), the sample substance S is captured on the working electrode 161 by the capture substance 10 immobilized on the surface of the working electrode 162. At this time, substances in the sample other than the sample substance S, that is, the substance (contaminant F) is not captured by the capture substance 10.

Note that in the present invention the capture substance 10 need not be used if the sample substance S can be specifically captured on the working electrode 161. For example, when ITO is used as the working electrode, a sample substance S containing a thiol group can be captured on the working electrode 161 without using a capture substance 10 by binding the ITO and the thiol group.

The capture substance 10 may be suitably selected according to the type of sample substance S. For example, if the sample substance S is a nucleic acid, the capture substance 10 may be a nucleic acid antibody or a nucleic acid probe which hybridizes to the nucleic acid. When the sample substance S is a protein or peptide, the capture substance 10 may be antibodies against such proteins or peptide, ligands against such proteins, and receptor proteins against such peptides.

Capturing the sample substance S with the capture substance 10 can be carried out, for example, under the condition that the sample substance S is bound to the capture substance 10. The condition of binding the sample substance S to the capture substance 10 can be suitably selected according to the type of sample substance S. For example, when the sample substance S is a nucleic acid and the capture substance 10 is a nucleic acid probe which hybridizes to the nucleic acid, capturing the sample substance S can be carried out under in the presence of a hybridization buffer solution. When the sample substance is a nucleic acid and the capture substance 10 is an antibody against the nucleic acid, capturing the sample substance S can be carried out in a solution suited to induce an antigen-antibody reaction, such as phosphate-buffered saline, HEPES buffer, PEPES buffer, tris buffer and the like.

Next, the labeled binder 20$a$ is injected into the inspection chip 120 from the sample injection inlet 130$b$. In this way the labeled binder 20$a$ is bound to the sample substance S captured on the working electrode 161 (refer to step (B), FIG. 13(B)). In step (B), a complex containing the capture substance 10, sample substance S, and labeled binder 20$a$ on the working electrode 161.

The labeled binder 20$a$ is configured by a binder 22 for binding to the sample substance S, and a modified labeled substance 23$a$ which includes a soluble carrier 21, labeled substance 24$a$, and attractant modified substance 25. In the labeled binder 20$a$, the modified labeled substance 23$a$ and the binder 22 are immobilized on the surface of the soluble carrier 21.

The labeled substance 24$a$ releases electrons which are excited via irradiation with light. the labeled substance 24$a$ may be at least one items selected from groups of metal complexes, organic phosphors, quantum dots, and inorganic phosphors.

Examples of labeled substances include metal phthalocyanine, ruthenium, osmium complex, iron complex, zinc complex, 9-phenyl-xanthene dyes, cyanine dyes, cyanine metalloproteinases, xanthene dyes, triphenylmethane dyes, acridine dyes, oxazine dyes, coumarin dyes, merocyanine dyes, rhoda-cyanine dyes, polymethine dyes, porphyrin dyes, phthalocyanine dyes, rhodamine dyes, xanthene dyes, chlorophyll pigments, eosin dyes, mercurochrome dyes, indigo dyes, BODIPY dyes, CALFluor dyes, Oregon Green dyes, Rhodol Green, Tex. Red, Cascade Blue, nucleic acids (DNA, RNA and the like), cadmium selenide, cadmium telluride, $Ln_2O_3$:Re, $Ln_2O_2S$:Re, ZnO, $CaWO_4$, $MO.xAl_2O_3$:Eu, $Zn_2SiO_4$:Mn, $LaPO_4$:Ce, b, Cy3, Cy3.5, Cy5, Cy5.5, Cy7, Cy7.5, and Cy9 (manufactured by Amersham Biosciences); Alexa Fluor 355, Alexa Fluor 405, Alexa Fluor 430, Alexa Fluor 488, Alexa Fluor 532, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, Alexa Fluor 750, and Alexa Fluor 790 (manufactured by Molecular Probes); DY-610, DY-615, DY-630, DY-631, DY-633, DY-635, DY-636, EVOblue 10, EVOblue 30, DY-647, DY-650, DY-651, DY-800, DYQ-660 and DYQ-661 (manufactured by Dyomics); Atto425, Atto465, Atto488, Atto495, Atto520, Atto532, Atto550, Atto565, Atto590, Atto594, Atto610, Atto611x, Atto620, Atto633, Atto635, Atto637, Atto647, Atto655, Atto680, Atto700, Atto725, Atto740 (manufactured by Atto-TEC GmbH); VivoTagS680, VivoTag680 and VivoTagS750 (manufactured by VisEn-Medical) and the like. Note that Ln represents La, Gd, Lu, or Y; Re represents a lanthanide element, M represents an alkaline earth metal element, and x represents an integer from 0.5 to 1.5. For other examples of labeled substances refer to U.S. Patent Publication No. 2009/0294305, U.S. Patent Publication No. 5893999, and Japanese Patent Publication No. 2009-23993.

The attractant modified substance 25 may be, for example, a nucleic acid such as DNA, RNA and the like. Note that in the present invention the attractant modified substance 25 need not be used when the labeled substance 24$a$ is a substance which can be attracted to the working electrode.

In this case, when a nucleic acid is used as the attractant modified substance, the length of the nucleic acid has one base or more but less than 10,000 based, and preferably has 10 bases or more but less than 40 bases from the perspectives of the binding efficiency of the soluble carrier and attracting the modified labeled substance 23a (described later) to the working electrode 161.

The binder 22 also may be a substance for binding with the capture substance 10 at different parts and locations in the sample substance S. The binder 22 may be suitably selected according to the type of sample substance S. For example, if the sample substance S is a nucleic acid, the binder 22 may be a nucleic acid antibody or a nucleic acid probe which hybridizes to the nucleic acid. When the sample substance S is a protein or peptide, the binder 22 may be antibodies against such proteins or peptides, ligands against such proteins, and receptor proteins against such peptides.

The modified labeled substance 20a is preferably constituted of nucleic acid and labeled substance 24a for ease of attraction to the working electrode 161.

In step (B), the remainder of the labeled binder 20a which does not bind to the sample substance S is present in a free state within the inspection chip 120. Therefore a step of removing the free labeled binder 20a ("washing step"; refer to FIG. 13(C)) follows after step (B). In this way the characteristics of the detection results are improved. Note that the washing step need not be carried out. In the washing step, for example, ethanol or pure water may be used.

In the photoelectrochemical detection method, the soluble carrier 21 contained in the complex formed on the working electrode 161 is then dissolved to release the modified labeled substance 23a (step (C); refer to FIG. 13(D)).

The soluble carrier 21 may be a substance which can be dissolved to release the modified labeled substance 23a immobilized on the surface thereof. Useful examples of the soluble carrier 21 include metal micro particles of gold, silver, palladium, platinum, iridium, rhodium and the like; polymer micro particles such as polymers of polyethylene, polystyrene, polyacrylonitrile, nylon, ethylene-acrylic acid copolymer, styrene-acrylic acid ester, styrene cross-linked acrylic esters, polyacrylic acid crosslinked butyl methacrylate crosslinked polymethyl methacrylate crosslinked silicone resin, phenol resin, melamine formaldehyde, benzoguanamine formalin benzoguanamine melamine formaldehyde, polylactic acid, polyamide resin and the like; polymeric micelles formed of polymer compounds containing hydrophilic polymer chains such as fatty acids such as palmitate, oleate ions and the like or polyalkylene oxide, polymalic acid, polyaspartic acid, polyethylene glycol and the like and hydrophobic polymer chains of polyamino acid, polystyrene, polymethyl methacrylate; liposomes which are microscopic spherical particles that form when phospholipids are hydrated; porous particles consisting of polysaccharides such as agarose gel and the like.

Among these soluble carriers 21, gold nano particles (gold micro particles) are preferable from the standpoint of ease of handling.

Note that the soluble carrier 21 may be a carrier having multiple layers formed of different materials insofar as the modified labeled substance can be released by dissolving only part of the surface on which the modified labeled substance is immobilized. For example, carriers in which only gold nano particles are soluble among gold-iron oxide (magnetic) nano particles consisting of gold nano particles bound to the periphery of iron oxide (magnetic) nano particles.

Dissolving the soluble carrier 21 can be accomplished by a method in accordance with the type of soluble carrier 21 under conditions that do no cause deterioration of the electrodes (working electrode, counter electrode, reference electrode) and materials of the substrate bodies configuring the inspection chip 120. For example, the carrier 21 can be dissolved by heating the soluble carrier 21 when the carrier comes into contact with a liquid which can dissolve the soluble carrier 21 or the carrier 21 is melted by heating the soluble carrier 21.

When the soluble carrier 21 consists of gold particles, the soluble carrier 21 can be dissolved by oxidation dissolution of the metal under conditions which to not cause deterioration of the electrodes (working electrode, counter electrode, reference electrode) or materials of the substrate bodies constituting the inspection chip 120. When dissolving metal micro particles, a liquid containing alkali hydroxide, a liquid containing alkali cyanide, a liquid containing ferrocyanide salts, a liquid containing a mixture of halogen and halogen compounds may be used. For example, potassium hydroxide is a solvent which may be used as a liquid containing alkali hydroxide. A further example is an aqueous solution containing sodium cyanide (NaCN) and sodium hydroxide as a liquid containing alkali cyanide. Another example is a mixture of potassium cyanide and potassium ferrocyanide as a liquid containing ferrocyanide salts. A mixture of alkali iodide and iodine (for example, ammonium iodide) and a mixture of alkali bromide and bromine (for example, ammonium bromide) are examples of a mixture of halogen body and halide salts. Pure water, and organic solvents such as acetonitrile are examples of solvents which can be used in these solvents. For example, when metal micro particles are used as the soluble carrier 21, there are known liquids which are used as etching liquids and metal stripping liquids.

When the soluble carrier 21 consists of polymer micro particles, the soluble carrier 21 can be dissolved by bringing the soluble carrier 21 into contact with an organic solvent, and heating the soluble carrier 21 to a temperature that is higher than the melting point of the polymer constituting the soluble carrier 21 under conditions which do not cause deterioration of the electrodes (working electrode, counter electrode, reference electrode) and material of the substrate body configuring the inspection chip 120. Examples of useful organic solvents include acetonitrile, ether compounds, chloroform, benzene, toluene, acetone, methylene chloride, cyclopentanone and the like.

When the soluble carrier 21 consists of polymeric micelles or liposome carriers, the soluble carrier 21 may be dissolved by dilution in water, and ultrasound processing to disrupt the micelle structure.

When the soluble carrier 21 consists of porous micro particles, the soluble carrier 21 may be dissolved by heating the soluble carrier 21 to a temperature higher than the melting point of the polysaccharide gel constituting the soluble carrier 21.

When the soluble carrier 21 consists of gold nano particles (gold micro particles), the soluble carrier 21 can be easily dissolved using a liquid containing acetonitrile and iodide ions.

In the photoelectrochemical detection method, the modified labeled substance 23a is then attracted to onto the working electrode 161 (step (D); refer to FIG. 13(E)). In this way the modified labeled substance 23a released in step (C) migrates to the vicinity of the working electrode 161. Therefore, electron reception is further facilitated between the labeled substance 24a and the working electrode body 162 compared to when only the modified labeled substance 23a is released in step (C).

In step (D), a solvent ('referred to as "attractant") may be used to attract the modified labeled substance 23a to the vicinity of the working electrode 161. Attracting the modified labeled substance onto the working electrode 161 can be accomplished by using the hydrophobic interaction or hydrophilic interaction between the modified labeled substance 23a and the attractant and working electrode 161, or by an electrophoretic effect induced by applying a voltage to the working electrode 161 or the counter electrode 169.

The attraction process may be accomplished by, for example, 1) increasing the hydrophilic interaction or hydrophobic interaction between the modified labeled substance 23a and the working electrode by changing the hydrophobic/hydrophilic properties of the attractant (that is, attracting the modified labeled substance 23a to the working electrode 161 by a different polarity) (attraction method 1);
2) increasing the electrophoretic effect by applying a positive or negative voltage to the working electrode according to the electrical charge of the modified labeled substance 23a (that is, attracting the modified labeled substance 23a to the working electrode using the electrophoretic effect) (attraction method 2). Attraction method 1 and attraction method 2 may be used individually or in combination.

In attraction method 1, when the attractant modified substance 25 contains nucleic acid, the attractant liquid preferably contains chaotropic ions from the perspective of increasing the hydrophobic interaction or hydrophilic interaction between the modified labeled substance 23a and the working electrode 161 to attract the test substance to the vicinity of the working electrode 161.

Chaotropic ions include, for example, iodide ion, bromide ion, guanidine ion, thiocyanate ion, tribromo acetic acid ion, trichloroacetic acid ion, perchlorate ion, dichloroacetic acid ion, nitrate ion, chloride ion, acetate ion, barium ion, calcium ion, lithium ion, cesium ion, potassium ion, magnesium ion and the like.

When the attractant liquid contains chaotropic ions, the concentration of the chaotropic ions in the attractant liquid will differ depending on the type of chaotropic ion used. The concentration is usually 1.0 to 8.0 mol/L. When the chaotropic ion used is guanidine ion, the concentration of chaotropic ion in the attractant liquid is usually 4.0 to 7.5 mol/L When the chaotropic ion used is cyanate ion, the concentration of the chaotropic ion in the attractant liquid is usually 3.0 to 5.5 mol/L.

Note that when the labeled substance 24a or the attractant modified substance 25 contains nucleic acid (DNS, RNA), the modified labeled substance 23a can be attracted to the vicinity of the working electrode 161 using the principles of conventional nucleic acid extraction and purification methods.

Nucleic acid extraction and purification methods include methods using a liquid phase, and methods using a carrier for nucleic acid binding. Examples of methods using a liquid phase include extraction with phenol/chloroform (Biochimica et Biophysica acta, 1963 issue, Vol 72, pp. 619-629), alkali method SDS (Nucleic Acid Research, published in 1979, 7 Volume, pp. 1513-1523), and nucleic acids precipitated with ethanol in buffer containing guanidine hydrochloride (Analytical Biochemistry, 162, 1987, 463) and the like. Examples of methods of using a carrier for nucleic acid binding include a method of nucleic acid isolation and adhering to glass particles using glass particles and sodium iodide solution (Proc. Natl. Acad. Sci. USA, 76-2: 615-619, 1979), and a method using silica particles and chaotropic ions (e.g., J. Clinical. Microbiology, Issue 1990, Vol 28, pp. 495-503; JP Patent No. 2,680,462). In the method using chaotropic ions and silica particles, first, a sample is prepared by mixing the silica particles for binding nucleic acid with a solution containing chaotropic ions having the ability to release nucleic acid in a sample; the nucleic acid then binds to the silica particles. Next, the contaminants are removed by washing. Thereafter, the nucleic acid which was bound to the silica particles is recovered. According to this method, the nucleic acid can be rapidly and simply extracted. Moreover, this method not only extracts DNA, it also is suitable for extracting the more unstable RNA, and is very good in terms of obtaining nucleic acid of high purity.

When the modified labeled substance 23a contains nucleic acid as the labeled substance 24a or attractant modified substance 25, the modified labeled substance 23a can be attracted to the vicinity of the working electrode 161 using a solvent which is used in nucleic acid extraction and purification methods. In this case, use of guanidinium ion, iodide ion, bromide ion, thiocyanate ion, or a combination thereof is preferred as the chaotropic ion, and use of an electrode for binding nucleic acid is preferred as the working electrode (for example, indium oxide containing tin).

When the modified labeled substance 23a contains nucleic acid as the labeled substance 24a or the attractant modified substance 25, the attractant may also may contain a buffer solution as needed. The buffer solution may be a buffer solution that is commonly used to stably preserve nucleic acid. The buffer solution preferably has a buffering capacity in the neutral range, that is, a pH of 5.0 to 9.0, from the perspective of stably preserving the nucleic acid. Examples of useful buffering solutions include tris-hydrochloride, sodium tetraborate-hydrochloric acid, potassium dihydrogen phosphate-sodium tetraborate buffer and the like. The buffer solution concentration is preferably 1 to 500 mmol/L.

On the other hand, in attraction method 2, a positive or negative voltage is applied to the working electrode according to the electrical charge of the modified labeled substance 23a. Nucleic acids are negatively charged. Therefore, when the modified labeled substance 23a contains nucleic acid as the labeled substance 24a or the attractant modified substance 25, the modified labeled substance 23a can be attracted to the vicinity of the working electrode 161 by applying a positive voltage to the working electrode 161.

In the photoelectrochemical detection method, the test substance is detected by exciting the labeled substance 24a by irradiating light on the labeled substance 24a in the modified labeled substance 23a present on the working electrode 161 of the inspection chip 120, then measuring the resultant photocurrent (step (E); refer to FIG. 13(F)).

In step (E), when the attractant in step (D) was used, the attractant can be replaced by an electrolyte suited for electrochemical detection. In this case, the labeled substance 24a is electrochemically detected in the presence of the electrolyte.

Note that the attractant liquid has the property of supplying electrons to the labeled substance 24a in an oxidized state, and this attractant liquid also may be used directly in the detection process in step (E) when photoelectrochemcial detection of the labeled substance 24a is possible.

A solution containing an electrolyte consisting of a salt capable of supplying electrons to the labeled substance 24a in an oxidized state, an aprotic polar solvent, protic polar solvent or a mixture of a protic polar solvent and aprotic polar solvent may be used as the electrolyte. The electrolyte also may contain other constituent ingredients.

Examples of materials useful as the electrolyte include iodide, bromide, metal complexes, thiosulfate, sulfite, and mixtures thereof. Specific examples of the electrolyte include metal iodides such as lithium iodide, sodium iodide, potassium iodide, cesium iodide, and calcium iodide; iodized salts of quaternary ammonium compounds such as tetraalkylammonium iodide, pyridinium iodide, imidazolium iodide and the like; metal bromides such as lithium bromide, sodium bromide, potassium bromide, cesium bromide, and calcium bromide; bromide salts of quaternary ammonium compounds such as tetraalkylammonium bromide, and pyridinium bromide; metal complexes such as ferrocyanide salts, and ferricyanide ions; thiosulfates such as sodium thiosulfate, ammonium thiosulfate, potassium thiosulfate, and calcium thiosulfate; sulfites such as sodium sulfite, potassium sulfite, ammonium sulfite, iron sulfite, sodium bisulfite, and calcium sulfite; and mixtures thereof. Among these, tetrapropylammonium iodide and calcium iodide are preferable.

The electrolytic concentration of the electrolyte is preferably 0.001 to 15 M.

Water, and polar solvent composed of a mixture of water and liquid buffering component may be used as the protic polar solvent.

Aprotic polar solvents include nitriles such as acetonitrile ($CH_3CN$); carbonates such as propylene carbonate and ethylene carbonate, heterocyclic compounds such as 1,3-dimethyl-imidazolinone, 3-methyl-non-oxazolinyl, and dialkyl imidazolium salts; dimethyl formamide, dimethyl sulfoxide, sulfolane and the like. Among these aprotic polar solvents, acetonitrile is preferred. Aprotic polar solvents and protic polar solvents can be used individually or as a mixture thereof. The mixture of polar aprotic polar solvent and protic polar solvent is preferably a mixture of water and acetonitrile.

The irradiation of light on the labeled substance 24a can be carried out using a light source which emits light of a wavelength capable of inducing photoexcitation of the labeled substance 24a. This light source may be suitably selected according to the type of labeled substance 24a. Fluorescent light, black light, germicidal lamp, incandescent lamp, low pressure mercury lamp, high pressure mercury lamp, xenon lamp, mercury-xenon lamp, halogen lamp, metal halide lamp, LED (white LED, blue LED, green LED, red LED and the like), laser light (carbon dioxide gas laser, dye laser, semiconductor laser), sunlight and the like may be used as the light source. Among these light sources, fluorescent lamp, incandescent lamp, xenon lamp, halogen lamp, metal halide lamp, LED, laser, or sunlight are preferable. In the detection step, the labeled substance 24a also may be irradiated only with light of a specific wavelength using a splitter and bandpass filter as necessary.

When measuring the photocurrent originating in the labeled substance 24a, a measuring device provided with, for example, an ammeter, potentiostat, recorder, and calculator may be used.

In step (E), the amount of sample substance can be determined by quantifying the photocurrent.

2. Redox Current Electrochemiluminesence Detection Method

Figure 14:
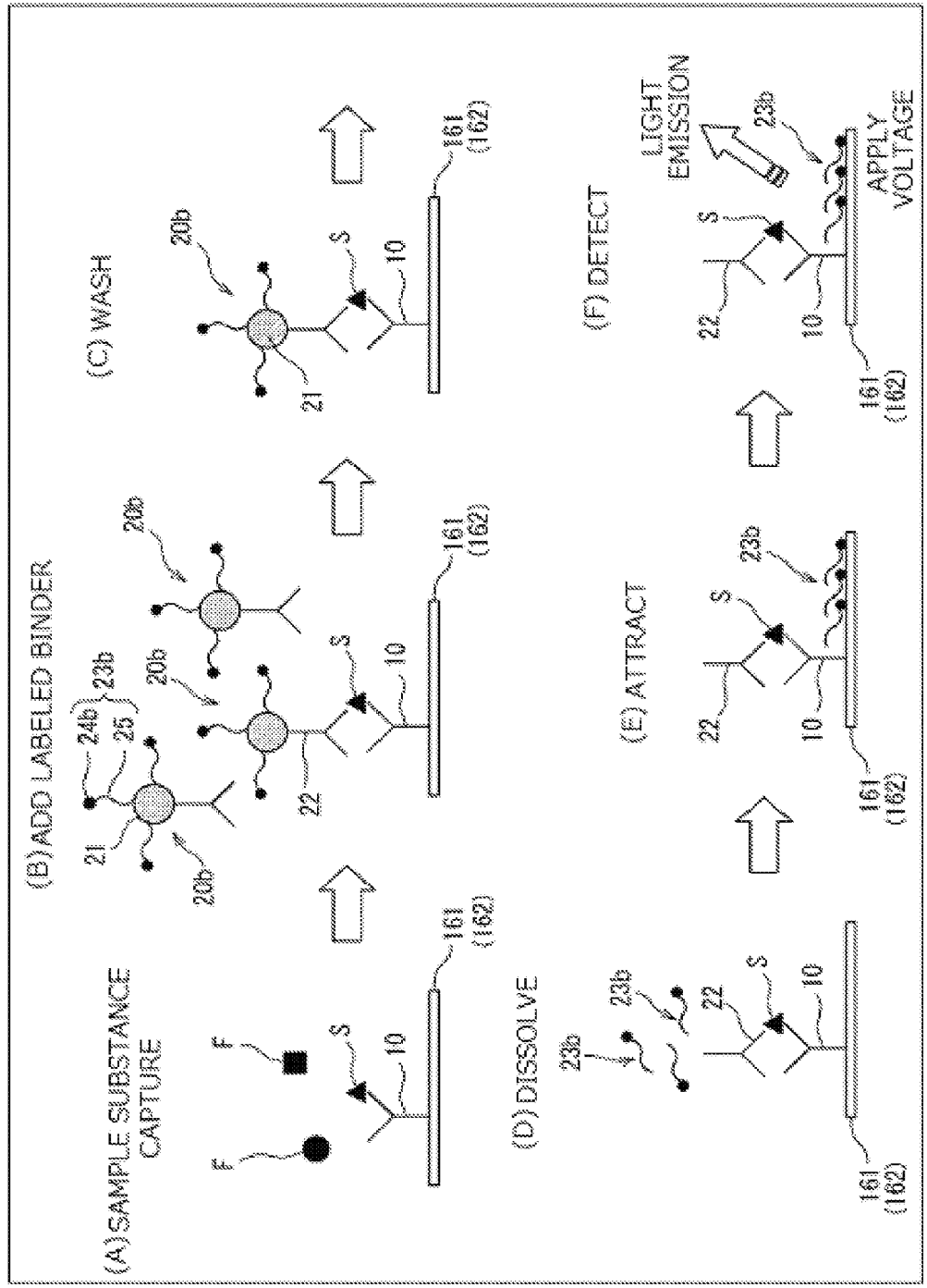
FIG. 14 is a process chart showing the processing sequence of another embodiment of the method of electrochemical detection (redox current electrochemiluminescence detection method) of a sample substance of the present invention.

The method of detection by redox electrochemiluminescence is described below. FIG. 14 is a process chart showing the processing sequence of another embodiment of the method of electrochemical detection (redox current electrochemiluminescence detection method) of a sample substance of the present invention.

Similar to the previously described photoelectrochemical detection method, in the redox current electrochemiluminescence detection method a sample containing the sample substance S is first injected into the inspection chip from the sample injection inlet 130b of the inspection chip 120. The sample substance S is then captured on the working electrode 161 (refer to step (A) and FIG. 14(A)). Next, the labeled binder 20b is injected into the inspection chip 120 from the sample injection inlet 130b. In this way the labeled binder 20a is bound to the sample substance S captured on the working electrode 161 (refer to step (B), FIG. 14(B)).

The labeled binder 20b is configured by a binder 22 for binding to the sample substance S, and a modified labeled substance 23b which includes a soluble carrier 21, labeled substance 24b, and attractant modified substance 25. The modified labeled substance 23b and the binder 22 are immobilized on the surface of the soluble carrier 21.

The labeled substance 24b emits light when a voltage is applied, or produces a redox current by application of a voltage.

The labeled substance which produces a redox current via application of a voltage may be, for example, a metal complex containing a central metal that causes an electrically reversible oxidation reduction reaction. Examples of useful metal complexes include tris(phenanthroline) zinc complex, tris (phenanthroline) complexes, ruthenium, tris(phenanthroline) cobalt complexes, di(phenanthroline) zinc complex, di(phenanthroline) ruthenium complex, di (phenanthroline) cobalt complexes, platinum complexes bipyridine, pyridine platinum target complexes, platinum-phenanthroline complex, tris(bipyridyl) zinc complex, tris(bipyridyl) ruthenium complex, tris(bipyridyl) cobalt complex, di(bipyridyl) zinc complex, di(bipyridyl) ruthenium complex, di(bipyridyl) cobalt complex and the like.

In the redox current electrochemiluminescence detection method, a labeled substance containing a nucleic acid may be used as the attractant modified substance. When a nucleic acid is used as the labeled substance 23b, a redox current derived from adenine, thymine, guanine, cytosine, or uracil may be used as the redox current.

Examples of useful labeled substance which emit light upon application of a voltage include luminol, lucigenin, pyrene, dipheylanthracene, rubrene and the like.

The light emission of the labeled substance may be enhanced, for example, by using luciferine derivatives such as firefly luciferine and dehydroluciferin, phenols such as phenylphenol and chlorophenol, and enhancers such as naphthols.

Note that the attractant modified substance 25 and the binder 22 are identical to the attractant modified substance 25 and the binder 22 used in the photoelectrochemical detection method.

In the redox current electrochemiluminescence detection method, the free labeled binder 20b is then removed (washing step; refer to FIG. 14(C)). The soluble carrier 21 contained in the complex formed on the working electrode 161 is then dissolved to release the modified labeled substance 23b (step (C); refer to FIG. 14(D)). Thereafter, the modified labeled substance 23b is attracted onto the working electrode 161 (step (D); refer to FIG. 14(E)). These steps may be carried out by the same operations as described in the photoelectrochemical detection method.

In the redox current electrochemiluminescence detection method, a voltage is then applied to the labeled substance 24b in the modified labeled substance 23b present on the working electrode 161 of the inspection chip 120. the sample substance S is then detected by measuring the light or the redox current based on the labeled substance 24b (step E; refer to FIG. 14(F)). Note that in FIG. 14(F) the example shows light measurement.

In step (E), when the attractant in step (D) was used, the attractant can be replaced by an electrolyte suited for electrochemical detection as necessary. In this case, the labeled substance 24b is electrochemically detected in the presence of the electrolyte.

When measuring the redox current in step (E), a measuring device provided with, for example, potentiostat, function generator, recorder, and calculator may be used to measure the redox current.

In this case, the amount of the sample substance S can be determined by quantifying the redox current.

When light is measured based on the labeled substance 24b in step (E), a photon counter or the like may be used to perform the light measurement. In this case, instead of the electrodes, detection may be carried out indirectly using optical fiber electrodes obtained by forming transparent electrodes on the chip of optical fiber (refer to U.S. Pat. Nos. 5,776,672 and 5,972,692).

EXAMPLES

Although the present invention is described in detail below by way of examples, the present invention is not limited to these examples.

Fabrication Example 1

The working electrode body constituted by a thin film (200 nm thickness) of tin-doped indium oxide was formed on a substrate body of silicon dioxide ($SiO_2$). The thin film performs as both a conductive layer and an electron acceptor layer. Then, a working electrode lead for connecting an ammeter was connected to the working electrode body.

Surface treatment was carried out using the silane coupling agent 3-mercaptopropyl triethoxysilane (MPTES) on the surface of the working electrode body of the working electrode substrate. Next, as a capture substance, anti-mouse IgG antibody F (ab') 2 fragments (DAKO) were subjected to reduction treatment by TCEP (tris(2-carboxyethyl)phosphine), and the capture substance was immobilized on the surface of the working electrode by reaction with the MPTES of the surface of the working electrode body to form disulfide bonds. Thereafter, the blocking agent PEG thiol (Sigma-Aldrich) was reacted with the remaining MPTES on the surface of the working electrode body. In this way a working electrode substrate was obtained.

Fabrication Example 2

A counter electrode substrate was obtained by forming a counter electrode of a platinum thin film (conductive layer) 200 nm in thickness on a substrate body of silicon dioxide ($SiO_2$) by spattering. A counter electrode lead for connecting an ammeter was connected to the counter electrode. In this way a counter electrode substrate was obtained.

Fabrication Example 3

Figure 15A:
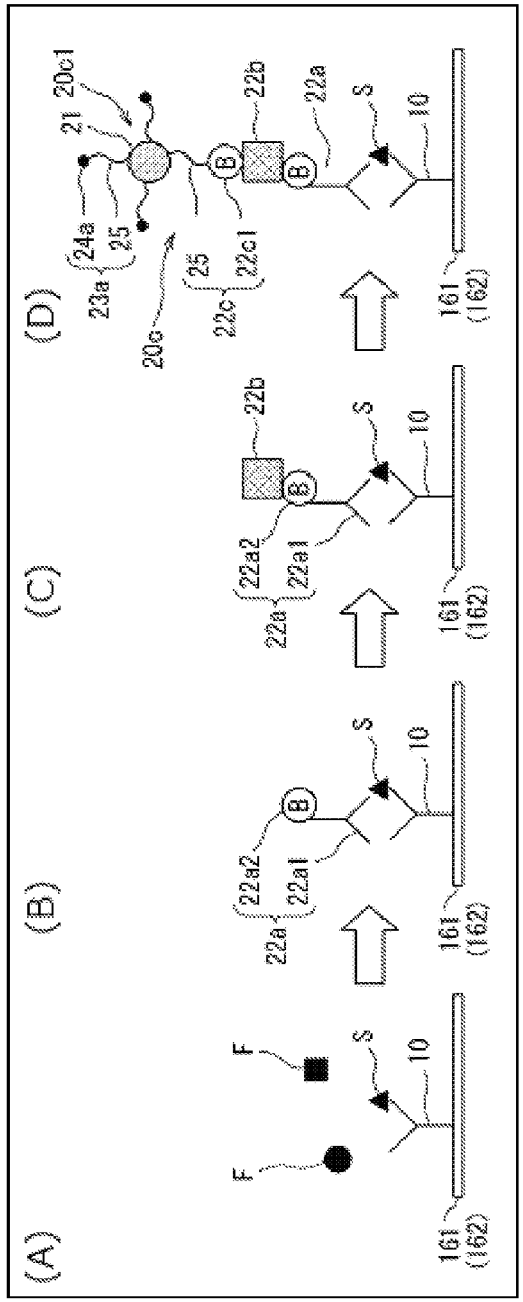
FIG. 15A is a brief illustration showing the operation sequence of the method of Experiment No. 1, Test No. 1.

A complex ("23a" in FIG. 15A(D)) composed of DNA having a length of 24 nucleotides with thiolated 3' termini ("25" in FIG. 15A(D); referred to as "attractant modified substance 25" below) and AlexaFluor750 (manufactured by Invitrogen; "24a" in FIG. 15A(D); referred to as "labeled substance 24" below) was used as a modified labeled substance.

Next, the modified labeled substance 23a was mixed with biotinylated DNA having a length of 24 nucleotides with thiolated 3' termini ("22c" in FIG. 15A(D); referred to as "first binder 22C" below) in a ratio of 10:1 (molar ratio). Note that the first binder 22c is composed of biotin and DNA having a length of 24 nucleotides ("22c1" in FIG. 15A(D)).

Mixing 560 picomoles of the obtained mixture and 5.6 picomoles of gold nano particles as a soluble carrier bonded the thiol groups of the respective modified labeled substance 23a and the first binder 22c to the surface of the soluble carrier 21. The obtained product was concentrated and purified by ultrafiltration to obtain the first modified binder 20c1. The obtained first modified binder 20c1 was added to a tris buffered solution (TBS-T) containing 0.1 vol % polyoxyethylene sorbitan monolaurate (Tween-20) and phosphate buffered saline and mixed to obtain a concentration of 1 nM and produce solution A.

Fabrication Example 4

Ascorbic acid was added as an electrolyte to the phosphate buffered saline (PBS) to obtain a 0.6 M concentration.

Fabrication Example 5

Acetonitrile and ethylene carbonate were mixed at a volume ratio of 2:3 to obtain an apriotic polar solvent. Tetrapropylammonium iodide was added as an electrolytic salt to the apriotic polar solvent to obtain a concentration of 0.6 M. Then, iodine was dissolved as a further electrolyte in the above obtained liquid to achieve a concentration of 0.06 M and obtain a dissolved attractant electrolyte.

Note that the iodine and tetrapropylammonium iodide can dissolve the gold nano particles. In addition, iodide ions generated from the iodine or tetrapropylammonium iodide can attract the modified labeled substance containing the first labeled binder to the working electrode. Therefore, dissolving the carrier used in the labeled binder, and attracting and electrochemically detecting modified labeled substance on the working electrode can be carried out in the same liquid using the dissolved attractant electrolyte obtained in fabrication example 4.

Experiment 1 silicone rubber (thickness 0.1 mm) was arranged as a partition to circumscribe the working electrode substrate and working electrode body obtained in fabrication example 1. Thereafter, 30 μL of sample containing mouse IgG (sample substance S) (composition: 1 μg mouse IgG/mL (tris-buffered solution containing 1 mass % bovine serum albumin (TBS-T)) was supplied into the space circumscribed by the silicone rubber and working electrode substrate, and the working electrode substrate was allowed to rest for 60 minutes at 25° C. In this way the sample substance S was captured by the capture substance 10 on the working electrode body 162 (refer to FIG. 15A(B)).

Next, 30 μL of solution B (composition: 4 ng biotin labeled anti-mouse IgG antibody (Sigma)/μL (tris-buffer solution containing 1 mass % bovine serum albumin (TBS-T)) containing biotin labeled anti-mouse IgG ("22a" in FIG. 15A(B); referred to as "second binder 22a" below) was introduced in the space of the working electrode substrate, and the working electrode substrate was allowed to rest for 30 minutes at 25° C. (refer to FIG. 15A(B)). In this way the second binder 22a was added to the sample substance S on the working electrode body 162 (refer to FIG. 15A(C)). Note that the second binder 22a is constituted by anti-mouse IgG antibody 22a1 for binding to the mouse IgG, and biotin 22a2.

Next, 30 μL steptavidin ("22b" in FIG. 15A(C); referred to as "third binder 22b" below; tris-buffer solution (TBS-T) containing solution C (400 nM streptavidin (manufactured by Vector) which included "22b") was introduced into the space, and the working electrode substrate was allowed to rest for 30 minutes at 25° C. Thereafter, 30 μL of solution A obtained in fabrication example 3 was introduced to the space, and the working electrode substrate was allowed to rest for 30 minutes at 25° C. In this way a complex containing the capture substance 10, sample substance S, and labeled binder 20c was formed on the working electrode (refer to FIG. 15A(D)). Thereafter, the working electrode substrate was washed using pure water and tris-buffer solution (TBS-T) (Test 1). The above operations were identically repeated with the exception that a sample which did not contain the sample substance S was used instead of the sample containing the sample substance S (Test 2).

Figure 15B:
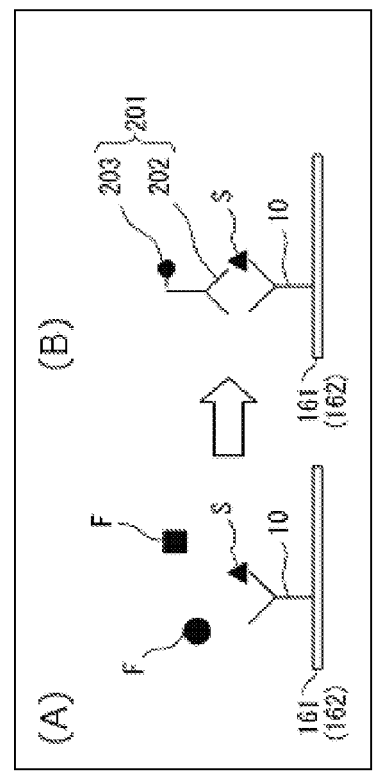
FIG. 15B is a brief illustration showing the operation sequence of the method of Experiment No. 1, Test No. 3.

Note that, as a control, the above operation were identically performed with the exception that 30 μL of solution D (composition: 4 ng AlexaFluor750 labeled anti-mouse IgG antibody (manufactured by Invitrogen)/μL (tris-buffer solution containing 1 mass % bovine serum albumin (TBS-T)) containing AlexaFluor750 labeled anti-mouse IgG antibody was used instead of the biotin labeled anti-mouse IgG antibody, streptavidin, and solution A obtained in fabrication example 3 (Test 3) (refer to FIGS. 15B (A) and (B)). The above operations were identically repeated with the exception that a sample which did not contain the sample substance S was used instead of the sample containing the sample substance S (Test 4).

Next, silicone rubber was arranged as a side wall 0.2 mm thick around the working electrode substrate. Then, 11.5 μL of the electrolyte obtained in fabrication example 4 was loaded into the space circumscribed by the silicone rubber and the working electrode substrate. The space filled with the electrolyte was then sealed from above the working electrode substrate by the counter electrode substrate obtained in fabrication example 2. Hence, the working electrode and counter electrode came into contact with the electrolyte. An ammeter was then connected to the working electrode lead and the counter electrode lead.

Light emitted from the light source (laser light source; wavelength of 781 nm, output 13 mW) irradiated from the working electrode substrate side toward the counter electrode substrate. The labeled substance was excited by the irradiation and emitted electrons. Hence, a current flowed between the working electrode and the counter electrode via electron transport to the working electrode.

Figure 16:
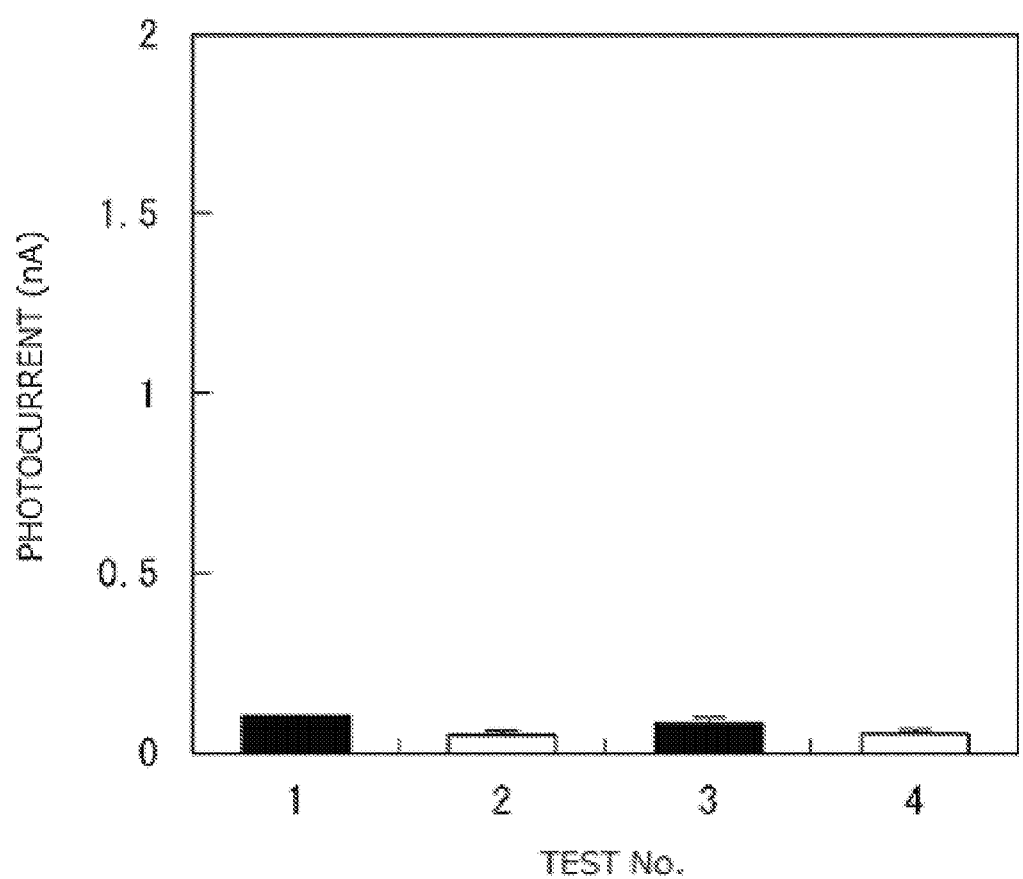
FIG. 16 is a graph showing photocurrent measurement results in the methods of Test Nos. 1 through 4 of Experiment No. 1.

This current was then measured. FIG. 16 shows the photocurrent measurement results for tests 1 through 4 of experiment 1.

Figure 17A:
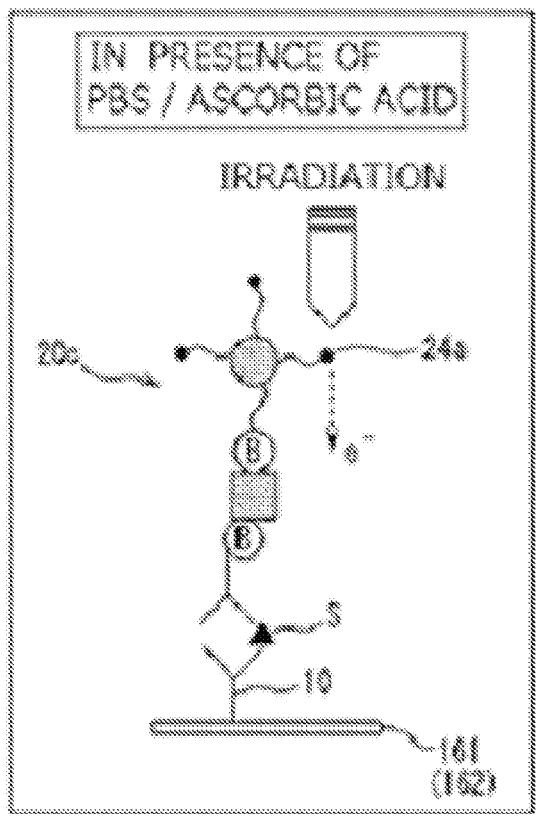
FIG. 17A is a brief illustration showing the state of the labeled substance during photocurrent measurement (detection step) in the method Test No. 1 in Experiment No. 1.
Figure 17B:
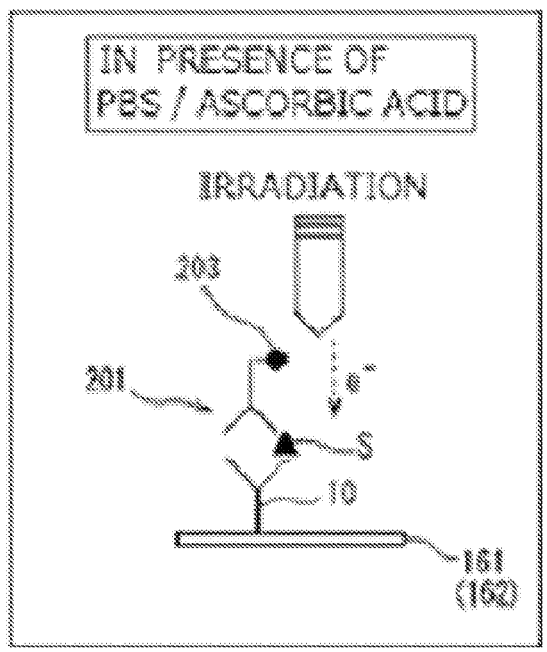
FIG. 17B is a brief illustration showing the state of the labeled substance during photocurrent measurement (detection step) in the method Test No. 3 in Experiment No. 1.

It can be understood from the results shown in FIG. 16 that when the electrolyte obtained in fabrication example 4 was used, a photocurrent could be detected based on the presence of the sample substance S in tests 1 and 3. However, there was a slight difference in the photocurrent when the sample substance S was not present (refer to tests 2 and 4 in FIG. 16). This is thought to be due to the difficulty of transporting electrons generated from the labeled substances 24a and 203 to the working electrode body 162 due to the long distance between the working electrode body 162 and the labeled substances 24a and 203 in the method of test 1 (refer to FIG. 17A) and the method of test 3 (refer to FIG. 17B), as shown in FIG. 17.

Experiment 2

Figure 18:
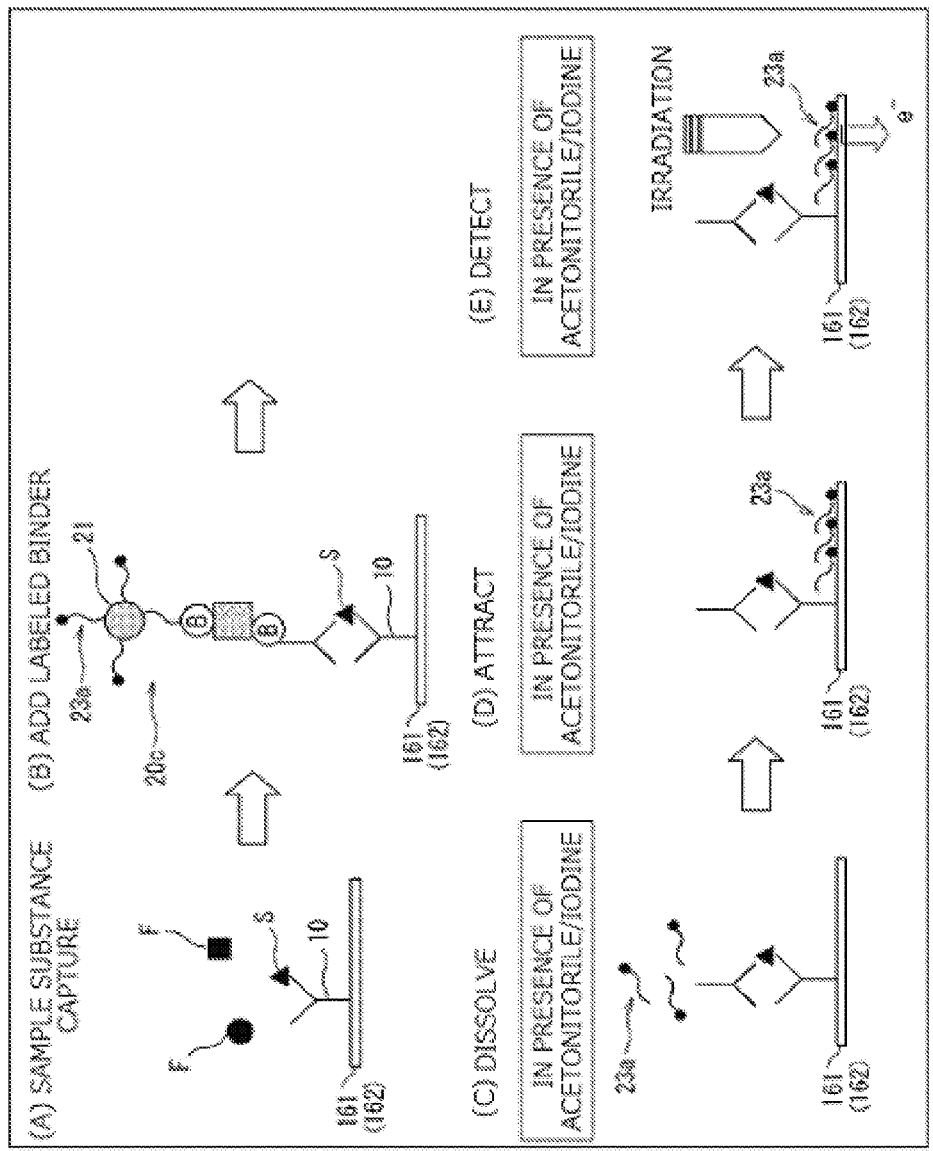
FIG. 18 is a brief illustration showing the operation sequence of the method used in Experiment No. 2, Test No. 5.

Silicone rubber (thickness 0.1 mm) was arranged as a partition to circumscribe the working electrode substrate and working electrode body obtained in fabrication example 1. Thereafter, 30 μL of sample containing mouse IgG (sample substance S) (composition: 1 μg mouse IgG/mL (tris-buffered solution containing 1 mass % bovine serum albumin (TBS-T)) was supplied into the space circumscribed by the silicone rubber and working electrode substrate, and the working electrode substrate was allowed to rest for 60 minutes at 25° C. In this way the sample substance S was captured by the capture substance 10 on the working electrode body 162 (refer to FIG. 18(A)).

Next, 30 μL of solution B containing biotin labeled anti-mouse IgG (second binder 22a) was introduced in the space of the working electrode substrate, and the working electrode substrate was allowed to rest for 30 minutes at 25° C. Then, 30 μL of solution C containing streptavidin (third binder 22b) was introduced in the space of the working electrode substrate, and the working electrode substrate was allowed to rest for 30 minutes at 25° C. Thereafter, 30 μL of solution A obtained in fabrication example 3 was introduced to the space, and the working electrode substrate was allowed to rest for 30 minutes at 25° C. In this way a complex containing the capture substance 10, sample substance S, and labeled binder 20c was formed on the working electrode (refer to FIG. 18(B)). Thereafter, the working electrode substrate was washed using pure water and tris-buffer solution (TBS-T) (Test 5). The above operations were identically repeated with the exception that a sample which did not contain the sample substance S was used instead of the sample containing the sample substance S (Test 6).

Note that, as a control, the above operations were identically repeated with the exception that 30 μL of solution D containing AlexaFluor750 labeled anti-mouse IgG antibody was used instead 30 μL of solution A obtained in fabrication example 3 with biotin labeled anti-mouse IgG antibody, streptavidin (test 7). The above operations also were identically repeated with the exception that a sample which did not contain the sample substance S was used instead of the sample containing the sample substance S (Test 8).

Next, silicone rubber was arranged as a side wall 0.2 mm thick around the working electrode substrate. Then, 11.5 μL of the dissolved attractant electrolyte obtained in fabrication example 5 was loaded into the space circumscribed by the silicone rubber and the working electrode substrate. The space filled with the dissolved attractant electrolyte was then sealed from above the working electrode substrate by the counter electrode substrate obtained in fabrication example 2. The working electrode substrate and the counter electrode substrate were then allowed to rest for 5 minutes. Hence, the working electrode and counter electrode came into contact with the dissolved attractant electrolyte. An ammeter was then connected to the working electrode lead and the counter electrode lead. Note that the soluble carrier 21 was dissolved by the dissolved attractant electrolyte obtained in fabrication example 5, and the modified labeled substance 23a was thereby released. The free modified labeled substance 23a was attracted onto the working electrode body 162 by the dissolved attractant electrolyte obtained in fabrication example 5.

Figure 19:
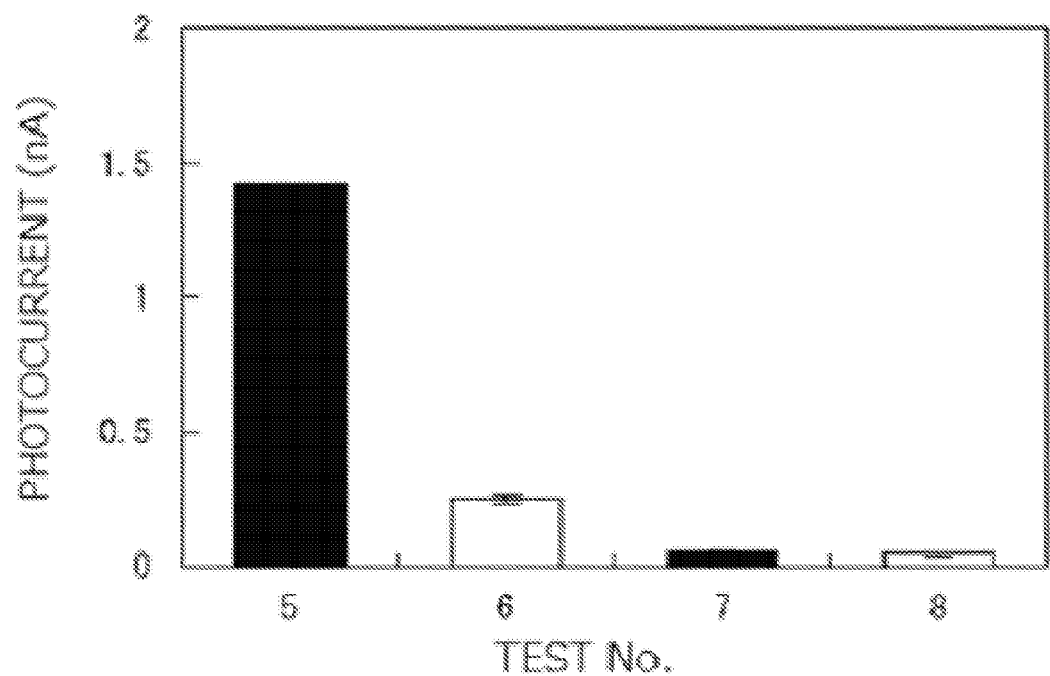
FIG. 19 is a graph showing photocurrent measurement results in the methods of Test Nos. 5 through 8 of Experiment No. 2.

Light emitted from the light source (laser light source; wavelength of 781 nm, output 13 mW) irradiated from the working electrode substrate side toward the counter electrode substrate, and the photocurrent was measured. FIG. 19 shows the photocurrent measurement results for tests 5 through 8 of experiment 2.

Figure 20A:
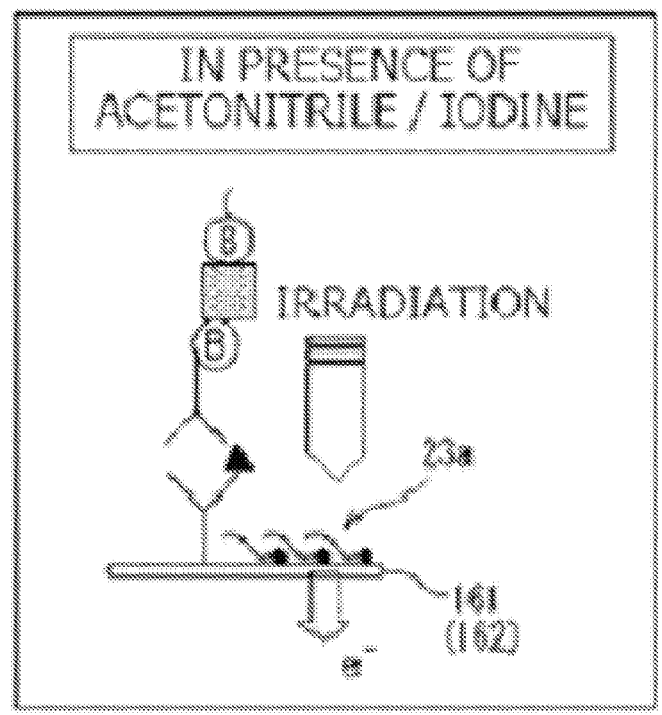
FIG. 20A is a brief illustration showing the state of the labeled substance during photocurrent measurement (detection step) in the method of Test No. 5 in Experiment No. 2.
Figure 20B:
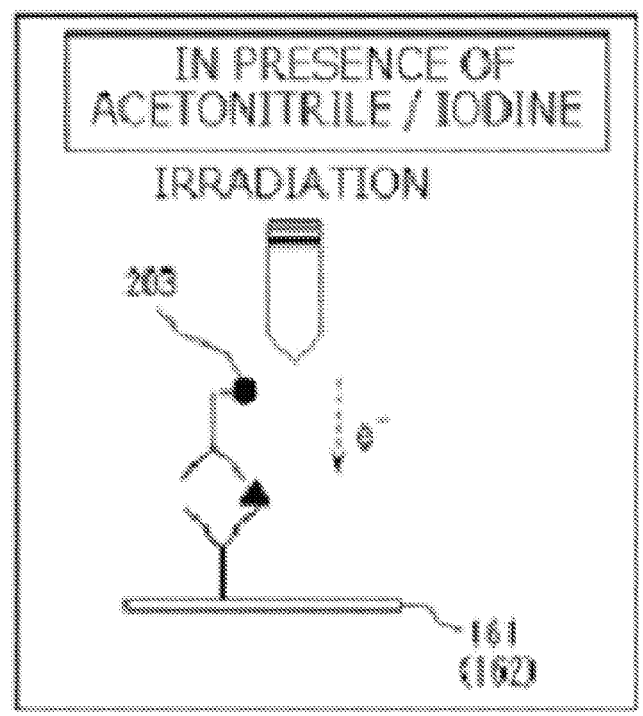
FIG. 20B is a brief illustration showing the state of the labeled substance during photocurrent measurement (detection step) in the method of Test No. 7 in Experiment No. 2.

It can be understood from the results shown in FIG. 19 that when the electrolyte obtained in fabrication example 5 was used, the photocurrent detected by the detection method of test 5 was larger than the photocurrent detected by the detection method of test 7. This is thought to be due to the ease of electron transport by attracting free modified labeled substance 23a to the working electrode body 162 and dissolving the soluble carrier 21 by dissolved attractant electrolyte obtained in fabrication 5 in the method of test 5 (refer to FIG. 20A) compared to the difficulty of transporting electrons generated from the labeled substance 203 to the working electrode body 162 due to the long distance between the working electrode body 162 and the labeled substances 203 due to physically bulky structure of the complex constituted by the capture substance, sample substance, and labeled substance in the method of test 7 (refer to FIG. 20B), as shown in FIG. 20.

Experiment 3

Silicone rubber (thickness 0.1 mm) was arranged as a partition to circumscribe the working electrode substrate and working electrode body obtained in fabrication example 1. Thereafter, 30 µL of sample containing mouse IgG (composition: 1 µg mouse IgG/mL (tris-buffered solution containing 1 mass % bovine serum albumin (TBS-T)) was supplied into the space circumscribed by the silicone rubber and working electrode substrate, and the working electrode substrate was allowed to rest for 30 minutes at 25° C.

Next, 30 µL of solution B containing biotin labeled anti-mouse IgG (second binder 22a) was introduced in the space of the working electrode substrate, and the working electrode substrate was allowed to rest for 30 minutes at 25° C. Then, 30 µL of solution C containing streptavidin (third binder 22b) was introduced in the space of the working electrode substrate, and the working electrode substrate was allowed to rest for 30 minutes at 25° C. Thereafter, 30 µL of solution A obtained in fabrication example 3 was introduced to the space, and the working electrode substrate was allowed to rest for 30 minutes at 25° C. Thereafter, the working electrode substrate was washed using pure water and tris-buffer solution (TBS-T) (Test 9). The above operations were identically repeated with the exception that a sample which did not contain the sample substance S was used instead of the sample containing the sample substance S (Test 10).

Note that, as a control, the above operations were identically repeated with the exception that 30 µL of solution D was used instead 30 µL of solution A obtained in fabrication example 3 with biotin labeled anti-mouse IgG antibody, streptavidin (Test 11). The above operations were identically repeated with the exception that a sample which did not contain the mouse IgG was used instead of the sample containing the mouse IgG (Test 12).

Next, silicone rubber was arranged as a side wall 0.2 mm thick around the working electrode substrate. Then, 11.5 µL of the dissolved attractant electrolyte obtained in fabrication example 5 was loaded into the space circumscribed by the silicone rubber and the working electrode substrate. The working electrode substrate was then allowed to rest for 5 minutes. Thereafter, the electrode substrate was washed in ethanol, dried, then the dissolved attractant electrolyte was replaced with the electrolyte obtained in fabrication example 4. The space filled with the electrolyte was then sealed from above the working electrode substrate by the counter electrode substrate obtained in fabrication example 2. Hence, the working electrode and counter electrode came into contact with the electrolyte. An ammeter was then connected to the working electrode lead and the counter electrode lead.

Figure 21:
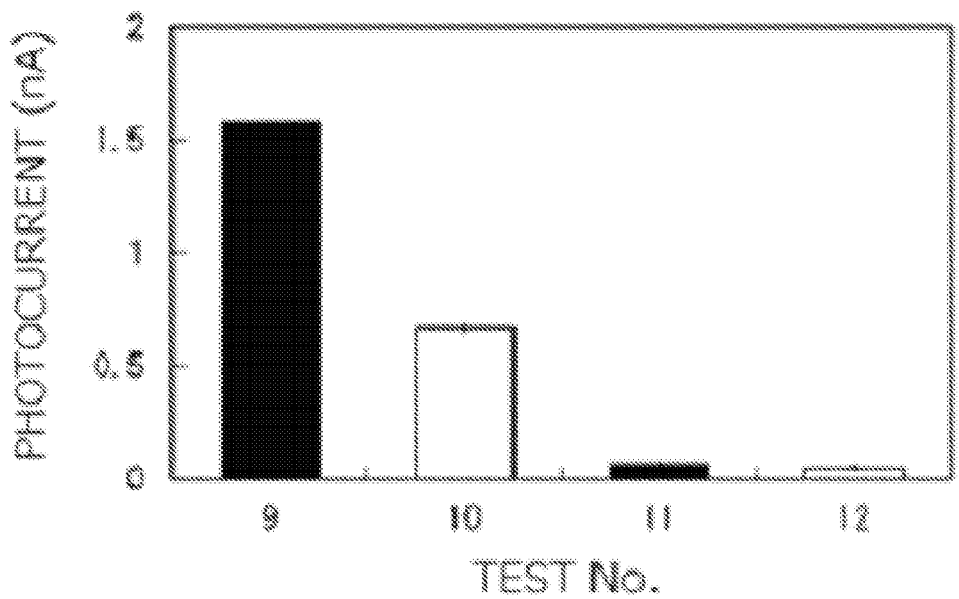
FIG. 21 is a graph showing photocurrent measurement results in the methods of Test Nos. 9 through 12 of Experiment No. 3.

Light emitted from the light source (laser light source; wavelength of 781 nm, output 13 mW) irradiated from the working electrode substrate side toward the counter electrode substrate, and the photocurrent was measured. FIG. 21 shows the photocurrent measurement results for tests 9 through 12 of experiment 3.

It can be understood from the results shown in FIG. 21 that the photocurrent detected by the detection method of test 9 was larger than the photocurrent detected by the detection method of test 11. These results indicate that when detecting the photocurrent, the modified labeled substance can be detected with high sensitivity even when the dissolved attractant electrolyte obtained in fabrication example 5 is replaced with the electrolyte obtained in fabrication example 4 by dissolving the soluble carrier and attracting the modified labeled substance to the working electrode body using the dissolved attractant electrolyte obtained in fabrication example 5. It can also be understood from these findings that the electrolyte obtained in fabrication example 4 has sufficient electrolytic properties when detecting a sample substance.

Experiment 4

The sample of test 13 and the sample of test 14 were obtained by dissolving labeled DNA of AlexaFluor750 having a length of 24 nucleotides in the dissolved attractant electrolyte obtained in fabrication example 5 (test 13) and in the electrolyte obtained in fabrication example 4 (test 14) to obtain a concentration of 1 nM, respectively. The dissolved attractant electrolyte obtained in fabrication example 5 has an action (attraction action) of attracting the AlexaFluor750 labeled DNA to the working electrode. On the other hand, the electrolyte obtained in fabrication example 4 does not have an attraction action.

11.5 µL of the sample of test 13 and 11.5 µL of the sample of test 14 were dripped onto a working electrode of the working electrode obtained in fabrication example 1, and allowed to rest for 5 minutes. Thereafter, the working electrode was washed with ethanol.

Figure 22:
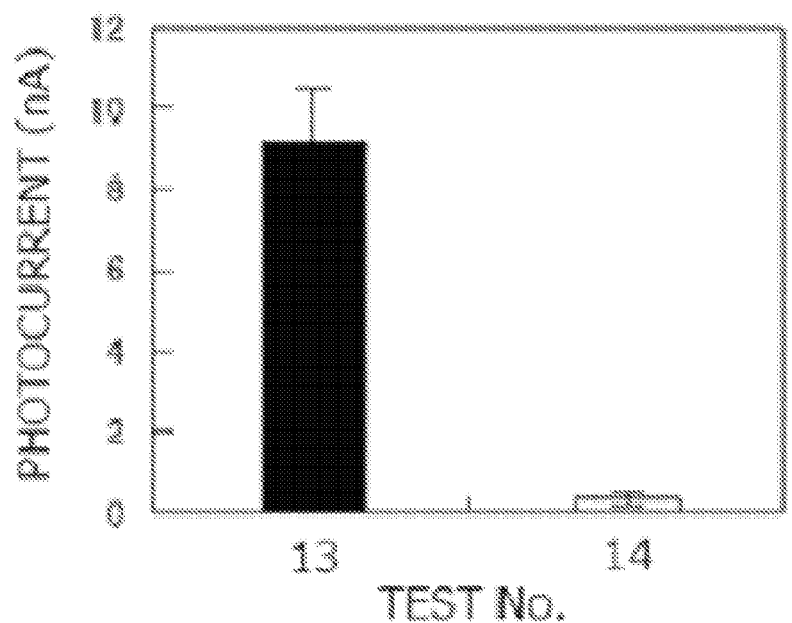
FIG. 22 is a graph showing the photocurrent measurement results when using the samples of Tests Nos. 13 and 14 in Experiment No. 4.

Next, silicone rubber was arranged as a side wall 0.2 mm thick around the working electrode substrate. Then, 11.5 µL of the dissolved attractant electrolyte obtained in fabrication example 5 was loaded into the space circumscribed by the silicone rubber and the working electrode substrate. The space filled with the dissolved attractant electrolyte was then sealed from above the working electrode substrate by the counter electrode substrate obtained in fabrication example 2. Thereafter, light emitted from the light source (laser light source; wavelength of 781 nm, output 13 mW) irradiated from the working electrode substrate side toward the counter electrode substrate, and the photocurrent was measured. FIG. 22 shows the photocurrent measurement results using the samples of tests 13 through 14 of experiment 4.

It can be understood from the results shown in FIG. 22 that the photocurrent was higher when using the sample of test 13 which contained the dissolved attractant electrolyte with attraction action than the photocurrent produced when using the sample of test 14 which included electrolyte that did not have an attraction action. Therefore, the step of attracting the modified labeled substance to the working electrode has the effect of improving the signal.

Fabrication Examples 6 Through 8

Figure 23A:
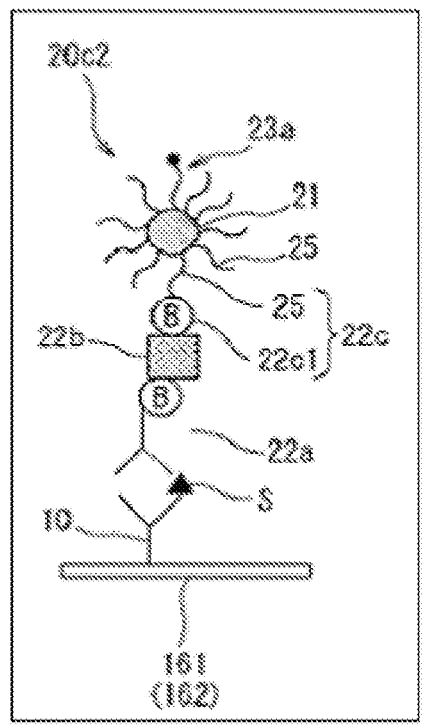
FIG. 23A is a brief illustration showing the state of the labeled substance during photocurrent measurements (detection step) when using a first modified binder obtained in fabrication example 6 in Experiment No. 5.
Figure 23B:
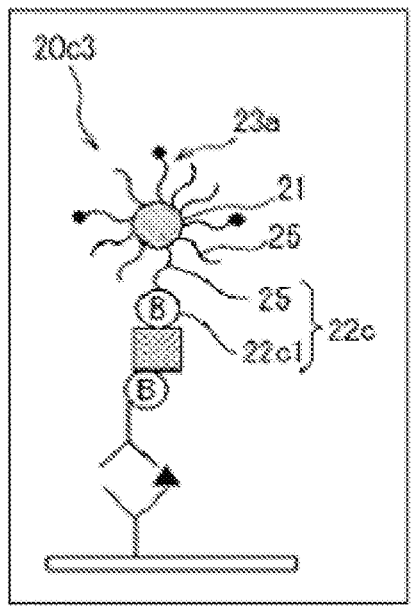
FIG. 23B is a brief illustration showing the state of the labeled substance during photocurrent measurements (detection step) when using a first modified binder obtained in fabrication example 7 in Experiment No. 5.
Figure 23C:
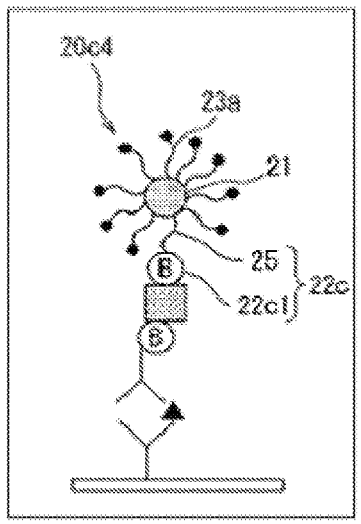
FIG. 23C is a brief illustration showing the state of the labeled substance during photocurrent measurements (detection step) when using a first modified binder obtained in fabrication example 8 in Experiment No. 5.

The first binder 22c, modified labeled substance 23a, and attractant modified substance 25 (DNA with a length of 24 nucleotides and thiolated 3' termini) were mixed in gold nano particles (soluble carrier 21) to achieve molar ratios of first binder 22c:modified labeled substance 23a:attractant modified substance 25 of 1:1:8 (fabrication example 6), 1:3:6 (fabrication example 7), and 1:9:0 (fabrication example 8), respectively, to obtain a first modified binder with an AlexaFluor750/biotin volume ratio of 1/1 ("20c2" in FIG. 23A; fabrication example 6), a first modified binder with an AlexaFluor750/biotin volume ratio of 3/1 ("20c3" in FIG. 23B; fabrication example 7), and a first modified binder with an AlexaFluor750/biotin volume ratio of 9/1 ("20c4" in FIG. 23C; fabrication example 8). The obtained first modified binder 20c2, first modified binder 20c3, and first modified binder 20c4 were respectively mixed with tris-buffer solution (TBS-T) containing 0.1 volume percent polyoxyethylene sorbitan monolaurate (Tween-20) to achieve a concentration of 1 nM and obtain solution A1 (fabrication example 6), solution A3 (fabrication example 7), and solution A4 (fabrication example 8).

Experiment 5 silicone rubber (thickness 0.1 mm) was arranged as a partition to circumscribe the working electrode substrate and working electrode body obtained in fabrication example 1. Thereafter, 30 μL of sample 1 (composition: 1 μg mouse IgG (sample substance S)/mL (tris-buffer containing 1 vol % bovine serum albumin (TBS-T)) or sample 2 (composition: 0 μg mouse IgG (sample substance S)/mL (tris-buffer containing 1 vol % bovine serum albumin (TBS-T)) was supplied to the space circumscribed by the silicone rubber and the working electrode substrate, and the working electrode substrate was allowed to rest for 60 minutes at 25° C.

Next, 30 μL of solution B containing biotin labeled anti-mouse IgG (second binder 22a) was introduced in the space of the working electrode substrate, and the working electrode substrate was allowed to rest for 30 minutes at 25° C. Then, 30 μL of solution C containing streptavidin (third binder 22b) was introduced in the space, and the working electrode substrate was allowed to rest for 30 minutes at 25° C. Thereafter, 30 μL of solution A2 obtained in fabrication example 6, 30 μL of solution A3 obtained in fabrication example 7, or 30 μL of solution A4 obtained in fabrication example 8 was introduced to the space, and the working electrode substrate was allowed to rest for 30 minutes at 25° C. Thereafter, the working electrode substrate was washed using pure water and tris-buffer solution (TBS-T).

Next, silicone rubber was arranged as a side wall 0.2 mm thick around the working electrode substrate. Then, 11.5 μL of the dissolved attractant electrolyte obtained in fabrication example 5 was loaded into the space circumscribed by the silicone rubber and the working electrode substrate. The space filled with the dissolved attractant electrolyte was then sealed from above the working electrode substrate by the counter electrode substrate obtained in fabrication example 2. The working electrode substrate and the counter electrode substrate were then allowed to rest for 5 minutes.

Figure 24:
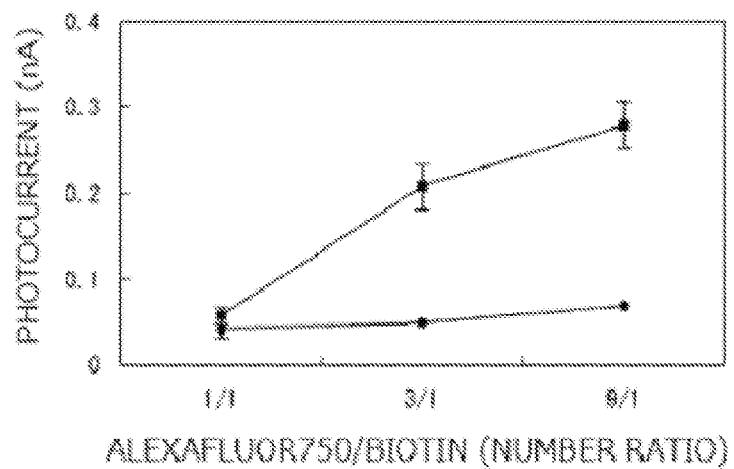
FIG. 24 is a graph showing the results of examining the relationship between AlexaFluor 750/biotin (volume ratio) and photocurrent in Experiment No. 5.

Light emitted from the light source (laser light source; wavelength of 781 nm, output 13 mW) irradiated from the working electrode substrate side toward the counter electrode substrate, and the photocurrent was measured. FIG. 24 shows the relationship between the photocurrent and the AlexaFluor750/biotin (volume ratio) in experiment 5. In the drawing, the black squares represent the photocurrent when sample 1 was used, and the black circles indicate the photocurrent when sample 2 was used.

It can be understood from the results shown in FIG. 24 that as the number of AlexaFluor750 labeled substance increases, the detected photocurrent increases. These findings show that the magnitude of the detected photocurrent corresponds to the amount of labeled substance according to the present method.

Experiment 6 silicone rubber (thickness 0.1 mm) was arranged as a partition to circumscribe the working electrode substrate and working electrode body obtained in fabrication example 1. Thereafter, 30 μL of sample 3 (composition: 3 n g mouse IgG (sample substance S)/mL (tris-buffer containing 1 vol % bovine serum albumin (TBS-T)), sample 4 (composition: 30 n g mouse IgG (sample substance S)/mL (tris-buffer containing 1 vol % bovine serum albumin (TBS-T)), or sample 5 (composition: 300 n g mouse IgG (sample substance S)/mL (tris-buffer containing 1 vol % bovine serum albumin (TBS-T)) was supplied to the space circumscribed by the silicone rubber and the working electrode substrate, and the working electrode substrate was allowed to rest for 60 minutes at 25° C.

Next, 30 μL of solution B containing biotin labeled anti-mouse IgG (second binder 22a) was introduced in the space of the working electrode substrate, and the working electrode substrate was allowed to rest for 30 minutes at 25° C. Then, 30 μL of solution C containing streptavidin (third binder 22b) was introduced in the space, and the working electrode substrate was allowed to rest for 30 minutes at 25° C. Thereafter, 30 μL of solution A3 obtained in fabrication example 5 was introduced to the space, and the working electrode substrate was allowed to rest for 30 minutes at 25° C. Thereafter, the working electrode substrate was washed using pure water and tris-buffer solution (TBS-T).

Next, silicone rubber was arranged as a side wall 0.2 mm thick around the working electrode substrate. Then, 11.5 μL of the dissolved attractant electrolyte obtained in fabrication example 5 was loaded into the space circumscribed by the silicone rubber and the working electrode substrate. The space filled with the dissolved attractant electrolyte was then sealed from above the working electrode substrate by the counter electrode substrate obtained in fabrication example 2. The working electrode substrate and the counter electrode substrate were then allowed to rest for 5 minutes.

Figure 25:
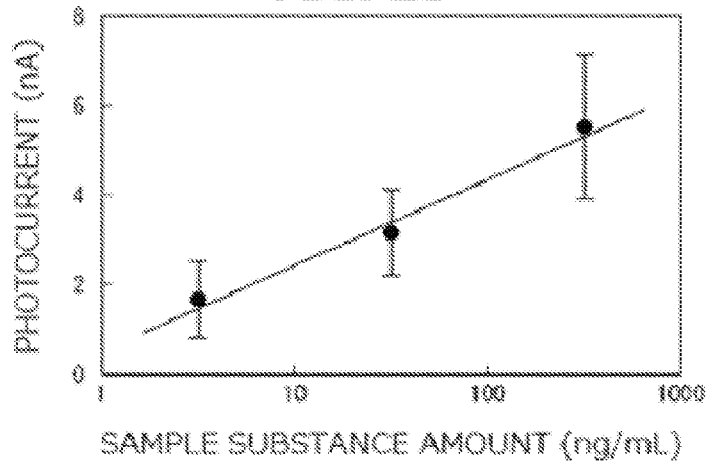
FIG. 25 is a graph showing the results of examining the relationship between the amount of sample substance and photocurrent in Experiment No. 6.

Light emitted from the light source (laser light source; wavelength of 781 nm, output 13 mW) irradiated from the working electrode substrate side toward the counter electrode substrate, and the photocurrent was measured. FIG. 25 shows the relationship between the photocurrent and the amount of sample substance in experiment 6.

It can be understood from the results shown in FIG. 25 that as the sample substance increases, the detected photocurrent increases. These findings show that the sample substance can be quantified by the present method.

What is claimed is:

1. A method of electrochemically detecting a sample substance, comprising:
    contacting and capturing a sample containing a sample substance on a working electrode;
    forming a complex including the sample substance and a capture substance on a working electrode by bringing the sample substance into contact with a labeled binder comprising a binder for binding to the sample substance and a soluble carrier bound to a modified labeled substance containing a labeled substance and a nucleic acid, on a working electrode possessing the captured sample substance;
    isolating the modified labeled substance by dissolving the soluble carrier contained in the complex formed on the working electrode;

attracting the modified labeled substance onto the working electrode; and electrochemically detecting the labeled substance in the modified labeled substance.

2. The method of claim 1, wherein the nucleic acid is DNA or RNA.

3. The method of claim 1, wherein the modified labeled substance is attracted to the working electrode by a difference in polarity in the attraction step.

4. The method of claim 3, wherein the difference in polarity is produced by a liquid containing chaotropic ions.

5. The method of claim 4, wherein at least one chaotropic ion is selected from groups of iodide ion, bromide ion, guanidine ion, thiocyanate ion, tribromo acetic acid ion, trichloroacetic acid ion, perchlorate ion, dichloroacetic acid ion, nitrate ion, chloride ion, acetate ion, barium ion, calcium ion, lithium ion, cesium ion, potassium ion, magnesium ion.

6. The method of claim 1, wherein the soluble carrier is dissolved by a solvent for dissolving the soluble carrier in the release step.

7. The method of claim 6, wherein the soluble carrier is a metal to be dissolved in the solvent, or alloy thereof.

8. The method of claim 7, wherein the soluble carrier is a gold nano particle.

9. The method of claim 6, wherein the solvent comprises iodine or iodide.

10. The method of claim 1, wherein the soluble carrier is a carrier which melts when heated; and the soluble carrier is dissolved by heating the soluble carrier in the release step.

11. The method of claim 1, wherein the labeled substance in the modified labeled substance is electrochemically detected in the presence of an electrolyte in the detection step.

12. The method of claim 1, wherein the release step, attraction step, and detection step are carried out in a liquid comprising iodide ions and acetonitrile.

13. The method of claim 1, wherein washing is performed to remove the free labeled binder after the formation step.

14. The method of claim 1, wherein the working electrode comprises a working electrode body, and the capture substance for capturing the sample substance, the capture substance being immobilized on the working electrode body.

* * * * *